(12) United States Patent
Stroup

(10) Patent No.: US 8,603,047 B2
(45) Date of Patent: Dec. 10, 2013

(54) DEVICES, ASSEMBLIES AND METHODS FOR CONTROLLING FLUID FLOW

(75) Inventor: David Karl Stroup, El Cajon, CA (US)

(73) Assignee: Infusion Innovations, La Jolla, CA (US)

( * ) Notice: Subject to any disclaimer, the term of this patent is extended or adjusted under 35 U.S.C. 154(b) by 58 days.

(21) Appl. No.: 13/308,076

(22) Filed: Nov. 30, 2011

(65) Prior Publication Data
US 2012/0157914 A1 Jun. 21, 2012

Related U.S. Application Data

(60) Provisional application No. 61/423,204, filed on Dec. 15, 2010, provisional application No. 61/511,457, filed on Jul. 25, 2011.

(51) Int. Cl.
A61M 5/00 (2006.01)

(52) U.S. Cl.
USPC ............................ 604/246; 604/207; 604/256

(58) Field of Classification Search
USPC ......... 604/187, 188, 207, 236, 237, 238, 246, 604/247, 248, 249, 256, 533, 537
See application file for complete search history.

(56) References Cited

U.S. PATENT DOCUMENTS

| 3,931,992 | A | 1/1976 | Coel |
| 4,694,856 | A | 9/1987 | Leibinsohn |
| 5,242,393 | A | 9/1993 | Brimhall et al. |
| 5,255,734 | A | 10/1993 | Leonard et al. |
| 5,755,269 | A | 5/1998 | Venooker et al. |
| 6,364,869 | B1 * | 4/2002 | Bonaldo ....................... 604/537 |
| 7,815,614 | B2 | 10/2010 | Fangrow, Jr. |
| 2003/0199835 | A1 | 10/2003 | Leising |
| 2004/0172006 | A1 | 9/2004 | Bonaldo |
| 2007/0088293 | A1 | 4/2007 | Fangrow |
| 2007/0120083 | A1 | 5/2007 | Simpson et al. |
| 2011/0276035 | A1 * | 11/2011 | Fangrow et al. .............. 604/535 |

FOREIGN PATENT DOCUMENTS

| EP | 1827568 | * | 6/2006 |
| WO | 2009052433 | | 4/2009 |
| WO | 2009111596 | | 9/2009 |

OTHER PUBLICATIONS

International Search Report and Written Opinion for PCT/US2009/36088 dated Mar. 4, 2009, 16 pages.
International Search Report and Written Opinion for PCT/US2011/040583 dated Feb. 23, 2012, 10 pages.
Notification, International Search Report and Written Opinion dated Jul. 30, 2012 from PCT/US2011/064488.

* cited by examiner

Primary Examiner — Theodore Stigell
(74) Attorney, Agent, or Firm — Stephen C. Beuerle; Procopio Cory Hargreaves & Savitch LLP

(57) ABSTRACT

A valve is provided for controlling flow along a fluid line that includes an outer shell and an inner housing slidably disposed therein that includes connector threads surrounding a boss on one end and a passage through the boss. A backing member is coupled to the outer shell and has a sealing pin extending into the passage. A connector may be threaded into the one end of the inner housing, thereby slidably engaging the connector threads, causing the inner housing to move helically from a closed position wherein the sealing pin engages an outlet opening at the distal end of the boss to seal the outlet opening and an open position wherein the inner housing is directed away from the sealing pin to open a fluid path through the valve, around the pin, and through the outlet opening.

52 Claims, 29 Drawing Sheets

DEVICES, ASSEMBLIES AND METHODS FOR CONTROLLING FLUID FLOW

RELATED APPLICATION

The present invention claims the benefit of U.S. provisional pat. app. No. 61/423,204 filed on Dec. 15, 2010 and U.S. provisional pat. app. No. 61/511,457 filed on Jul. 25, 2011, the contents of which are incorporated herein by reference in their entirety.

FIELD OF THE INVENTION

The present invention relates generally to apparatus and methods for controlling flow. More particularly, the present invention relates to devices, assemblies, and/or methods for controlling fluid flow, e.g., to connectors and/or valves for controlling flow through an IV or other fluid line into a patient, a syringe, container, and/or other medical device, and/or to systems including such connectors and/or valves.

BACKGROUND OF THE INVENTION

Controlling flow is an important and useful tool in virtually all scientific fields. One such field where controlling flow is highly useful is in the medical arena. For example, it may be useful to control flow during infusion, e.g., when introducing fluid into a blood vessel, such as a vein, via a fluid line for therapeutic and/or diagnostic purposes. The fluid introduced may be saline solution, plasma solution, glucose solution, antibiotics, pain relievers, nuclear medicine agents, and the like. Infusion may involve many fluid doses into a patient over long periods of time. Early in the infusion field, each fluid dose required a new needle to be inserted into the vein. Repeated insertion of a needle into the same vein of a patient, however, may damage the vein, increase the potential for bruising, and/or inflict pain on or discomfort to the patient.

Health professionals quickly changed this routine by inserting one needle into the patient's vein, and leaving it there for initial and subsequent fluid dose introductions. This stationary needle could be connected to a first or proximal end of a catheter that had an opening at a second or distal end for receiving fluid from a syringe or other device. For example, a latex cap was placed over the distal end of the catheter, which could be penetrated by a beveled hollow needle. Once inserted into the patient's vein, the stationary needle could be secured with tape, but was prone to disconnection from the patient. From this basic concept, a range of needleless connectors were developed capable of linking the fluid line to the patient's catheter directly thereby bypassing needle use. Further industry directive and federal regulation encouraged this alternative technique of promoting needleless connectors' use, thereby promoting removal of sharp instruments from the patient area.

Early needleless connectors featured a split septum on the female end (e.g., the end closer to the patient during connection). The split septum could be opened by inserting a cannula. The male end featured a blunt cannula, which was inserted into the split-septum on the female end. This method relieved some of the disconnection problems, but a new problem emerged. Removing the blunt cannula created a negative pressure inside the catheter, which caused a small amount of blood from the patient to flow into the proximal end of the catheter. These small amounts of blood would accumulate in the catheter, thereby clogging the fluid pathway. The consequence of this negative pressure, or negative bolus effect, was to require a new, clean catheter. The replacement of these clogged catheters may be expensive and/or painful to the patient.

The split septum on the female end was then replaced with an anti-reflux valve activated by the use of a male-female Luer configuration, also termed sequential valving. This male-female Luer connection has been standardized by the industry, e.g., through international standard ISO 594-2 "Conical fittings with a 6% (Luer) taper for syringes, needles and certain other medical equipment", Part 2: Lock fittings.

The demand for closed needleless systems for fluid administration is driven, at least partially, by the safety concerns associated with medications that are toxic to healthcare workers that prepare and administer these medications. These medications include chemotherapy and radiotherapeutic agents. Key industry organizations, such as the National Institute for Occupational Safety and Health (NIOSH), Oncology Nursing Society (ONS), and American Society of Health System Pharmacists (ASHP), recommend adopting closed systems to minimize drips, leaks, or spills of the drug to help eliminate surface contamination and exposure.

The vast majority of the self-sealing medical connectors that are used for the administration of parenteral fluids are designed with an unsealed male Luer connector on the end that remains connected to the patient's IV line, fluid source, etc., and a female connector on the opposite free end of the connector through which a syringe or other types of devices is connected. In many devices on the market, there is a self sealing valve built into the female connector. The male Luer typically does not have an internal valve, and as such, any remaining fluid is capable of being exposed to care providers and/or patients upon disconnection of the unsealed male Luer. As mentioned above, for certain applications, the fact that residual volume of the fluid may be unsealed and/or exposed to individuals around the IV system may pose significant health hazards. Additionally, these conventional Luer connectors may have a larger internal volume in which fluid may collect, and also employ many parts thereby increasing the potential for error in manufacturing or during use.

The standard connection mechanism for these Luer connectors involves aligning the threads together by a helical threading action. This threading action is meant to establish a connection between (e.g., engage) the two Luer ends, and is not the force used to open or close (e.g., actuate) fluid pathways. As the two Luer connectors are being connected together, there is a separate translational (e.g., on a vertical axis) action within these connection assemblies that acts to engage the fluid pathways. Traditionally, the female end has a thread on the outside while the male has a thread on the inside. Since most female ends have self-sealing valves, the user may open the fluid path with the translational force during engagement or after the male end is completely engaged and locked inside the female end. Thus, the user may not know at what point the fluid path is sufficiently opened or closed during connection and disconnection of the two connectors. The user only knows that the fluid path is closed (e.g., the two connectors are deactuated), when the two connectors are completely disengaged, or disconnected, and separated.

Conventional devices and assemblies for establishing medical connections are not completely effective and are potentially unsafe. For example, conventional medical connectors may expose the user to harmful agents during disconnection as a result of undesired bolus effects, may collect undesired fluid within their internal volumes after disconnection, may not notify the user of the actuation status during connection and disconnection, and/or may include many parts thereby making manufacture expensive.

Thus, there is a need in the art for a connector and/or connecting assembly that may effectively avoid uncertainty in the actuation process, avoid certain undesired pressure effects, create certain desired pressure effects, reduce the internal volume of the assemblies, and/or decrease the number of members required for manufacturing.

SUMMARY OF INVENTION

The present invention is directed to apparatus and methods for controlling flow through a fluid line or device, for example, to connectors and/or valves for delivering fluid via an intravenous ("IV") or other medical fluid line into a patient, a syringe, container, and/or other medical device, and to systems including such connectors and/or valves. Embodiments described herein may use fewer parts than conventional fluid flow devices for delivering fluid via a medical fluid line, may minimize and/or eliminate residual fluid within the connectors after disconnection, may utilize a rotational actuation force as opposed to translation force to avoid or create a desired bolus effect, and/or may incorporate actuation status indicators to notify the user when actuation is complete.

In exemplary embodiments, medical connectors disclosed herein may be used for the administration of parenteral fluids, such as needleless connectors that may offer alternative mechanisms to conventional Luer connectors, may utilize a visual indicator that provides instant feedback to an operator regarding actuation status, and/or may employ alternative ways for energy storage, including rotational force, electromagnetic, polymer torsion spring, and/or spring washers for actuation.

As used herein, "proximal" refers to a first end of the device and "distal" refers to a second opposite end of the device. For reference, the female end may be upstream in an IV flow circuit and the male may be downstream or vice versa. "Actuated" refers to the condition in which the fluid path is opened to allow fluid to transfer freely along the fluid path, while "deactuated" refers to the condition in which the fluid path is closed and fluid transfer is not permitted. "Engaged" refers to the condition in which two members that are designed for connection, for example, Luer connectors, are physically connected to each other in a manner in which they are designed to be connected, while "disengaged" refers to the condition in which two members, for example, Luer connectors, are physically disconnected from one another. When two members are referred to as "engaged," they may or may not be "actuated." The two members are "actuated" only when they are fully engaged, and fluid transfer is permitted between them. Alternatively, one member may use one valve component (male or female) and a passive (non-valved) element of opposite gender. "Female" Luer connector refers to a connecting member that includes a Luer thread on its outer surface. "Male" Luer connector refers to a connecting member that includes a Luer thread on its inner surface. "Passive" refers to the conditions under which a connector or assembly functions, and signifies that the assembly is capable of deactuating automatically as it is disengaged. "Non-Passive" refers to the conditions under which a connector or assembly functions, and signifies that the assembly does not automatically deactuate as it is disengaged, but requires a separate action. Optionally, in the embodiments herein, there may be sequential valving, resulting in co-dependent or independent actuation of male and/or female sides of valves.

In accordance with an exemplary embodiment, a valve is provided for controlling flow along a fluid line that includes an outer shell and an inner housing slidably or movably disposed therein that includes connector threads surrounding a boss on one end and a passage within the boss which has an outlet end opening. A backing member includes a base or hub which is coupled to the outer shell and has a connector portion at a first end for coupling to a component of a fluid line or to the outlet end of a syringe. In one embodiment, a sealing pin extends from a second end of the hub and into the passage through the boss. A connector may be threaded into the one end of the inner housing, thereby slidably engaging the connector threads, while camming elements on the inner housing cause the inner housing to move helically from a closed position wherein the sealing pin engages the boss to seal an outlet opening at the proximal end of the boss and an open position wherein the inner housing is directed away from the sealing pin to open a fluid path through the valve. In one embodiment, a fluid path is opened around the sealing pin and out through the open end of the boss when the inner housing moves to the open position.

The outer shell generally includes a first or proximal end, a second or distal end, and a passage extending therebetween. The inner housing is slidably disposed within the outer shell that includes a first or proximal end, a second or distal end adjacent the outer shell second end, and a passage extending therebetween and through the boss. The second end of the inner housing may include a connector including a set of connector threads surrounding the boss, e.g., defining a first helical axis, for connecting the valve to a fluid line. In an exemplary embodiment, the connector threads and boss may define a male Luer connector.

In one embodiment, the sealing pin is a solid member and has a tapered end portion or distal tip disposed within a tapered or reduced diameter outlet opening of the boss in the closed position of the valve. In the open position, the inner housing moves away from the sealing pin to open a passageway around the pin and through the open end of the boss. In one embodiment, cam features may be provided on the inner housing and the outer shell for limiting movement of the inner housing helically within the outer shell between a first or closed position wherein the sealing pin engages the boss to substantially seal the outlet end of the passageway through the boss and a second or open position wherein the inner housing is directed away from the sealing pin to create a passage around the sealing pin and out of the inner housing.

In one embodiment, the cam features may include a set of camming threads on the inner housing defining a second helical axis opposite the first helical axis, such that when a connector from a fluid line is threaded into the second end of the inner housing to engage the set of connector threads (e.g., along the first helical axis), the inner member is directed helically from the first position to the second position (e.g., along the second opposite helical axis) to open a fluid path through the valve, e.g., through the fluid passage, the annular passage within the boss around the sealing pin, and out through the outlet opening of the boss when the boss moves away from the sealing pin.

In one embodiment, the sealing pin may be formed from flexible material, e.g., silicone or other elastomeric material, for sealingly engaging the boss in the first position. In addition or alternatively, the hub or base may be formed from flexible material, e.g., integrally formed with or attached to the sealing pin, for slidably engaging the inner housing when the inner housing is directed between the first and second positions to provide a substantially fluid tight seal between the inner housing and the shaft. In addition or alternatively, an annular sealing member may be disposed in an annular recess in the hub or base, surrounding the sealing pin, for slidably engaging the inner housing when the inner housing is directed between the first and second positions to provide a substantially fluid tight seal between the inner housing and the sealing pin.

Optionally, the inner housing may be biased to the first position, thereby biasing the valve to close the fluid path. For example, the inner housing may be biased to the first position by providing a predetermined torque to the sealing pin, e.g., during assembly.

Optionally, the inner housing may include one or more status indicators, e.g., that provide a visual indication when the fluid path is open.

Optionally, a proximal connector may be provided at the proximal end of the backing member to couple the valve to a component of a fluid line, such as a syringe or other container, tubing, or the like. Alternatively, a length of tubing may be coupled to the backing member, e.g., including a first end extending through an opening in the outer shell first end and coupled to the backing member such that a lumen of the tubing is in fluid communication with the fluid passage through the valve. In one embodiment, the first end of the tubing may be substantially permanently attached to the backing member. Alternatively, the first end of the tubing may be removably attached to at least one of the backing member and the first end of the backing member.

Optionally, one or more components of the valve may include one or more coatings or other materials, e.g., for reducing infection. For example, at least one of the inner housing and the shaft may include anti-adhesive material, e.g., a coating on surfaces of the inner housing and shaft exposed along the fluid path, such as a hydrophilic coating and a coating of anti-fibronectin antibodies. In addition or alternatively, at least one of the inner housing and shaft may include an antimicrobial agent, e.g., a coating on surfaces of the inner housing and shaft exposed along the fluid path, such as a coating including a silver ion, one or more therapeutic antibiotics, minocylcine, rifampin, and tetracycline, or one or more surfaces may be impregnated with exidine or silver sulfadiazine, ultra low fouling zwitterionic-based material, and the like.

In accordance with another embodiment, an apparatus is provided for delivering fluid into a fluid line that includes a container including an enclosed interior with fluid therein and an outlet communicating with the interior; and a valve. The valve may include an outer shell comprising a first end coupled to the container adjacent the outlet, an open second end, and a passage extending therebetween; and an inner housing movably disposed within the outer shell and comprising a first end adjacent the outer shell first end, a second end adjacent the outer shell second end, and a passage extending therebetween, the second end comprising a set of connector threads surrounding a boss for connecting the valve to a fluid line, the connector threads defining a first helical axis, the inner housing passage extending through the boss to a reduced diameter outlet end opening of the boss. A base or backing member coupled to the first end of the outer shell includes a sealing pin disposed within the passage through the boss and in sealing engagement with the outlet end of the passage through the boss in a closed condition of the valve. Cam features on the inner housing and the outer shell limit movement of the inner housing helically within the outer shell between a first position wherein the sealing pin engages the boss to substantially seal the outlet and a second position wherein the inner housing is directed away from the sealing pin to create passage around the sealing pin through the outlet end of the boss. In one embodiment, the cam features comprise a set of camming threads on the inner housing defining a second helical axis opposite the first helical axis, such that when a connector from a fluid line is threaded into the second end of the inner housing to engage the set of connector threads, the inner member is directed helically from the first position to the second position to open a fluid path from the container interior through the annular passage within the boss around the sealing pin which is no longer in a sealing position in the outlet end of the boss.

In accordance with yet another embodiment, a method is provided for opening a fluid path in a fluid line using a valve including an outer shell, an inner housing movably disposed within the outer shell comprising a set of connector threads surrounding a boss on one end and a passage through the boss to an outlet end opening, and a base or backing member coupled to the outer shell having a sealing pin disposed within the passage through the boss, the inner housing movable between a first position in which the sealing pin is in sealing engagement with the outlet end of the boss, and a second position in which the outlet end of the boss is moved away from the corresponding end of the sealing pin and a fluid passage is formed between the boss and sealing pin and out through the outlet end of the passage through the boss. The fluid line may include a length of tubing or a syringe coupled to the backing member such that a lumen of the syringe or tubing communicates with the fluid passage, and a connector, e.g., coupled to tubing, a medical device, and the like, similar to other embodiments herein.

The connector may be threaded into the one end of the inner housing, thereby slidably engaging the connector threads with the connector and directing the inner housing from a first position wherein the sealing pin engages the boss to substantially seal the outlet opening in the boss and a second position wherein the inner housing is directed away from the sealing pin to open the outlet opening and provide a fluid passage within the boss and around the sealing pin through the outlet opening to open a fluid path through the valve and the connector.

In one embodiment, the connector threads defines a first helical axis, and the inner housing includes a set of camming threads defining a second helical axis opposite the first helical axis, such that when the connector is threaded into the inner housing to engage the set of connector threads, the inner member is automatically directed helically from the first position to the second position to open the fluid path.

After delivering fluid via the fluid line, the connector may be unthreaded from the one end of the inner housing, thereby directing the inner housing from the second position to the first position such that the sealing pin engages the boss to substantially seal the outlet opening of the boss and close the fluid path. Optionally, the inner housing may be biased to the first position such that, when the connector is unthreaded from the one end of the inner housing, the inner housing automatically returns to the first position. In addition or alternatively, the connector threads and camming threads may be configured such that, when the connector is unthreaded from the one end of the inner housing, the inner housing is directed to the first position before the connector is unthreaded from the connector threads.

Methods for using such connector and/or valve assemblies are also provided.

In a further embodiment, the valve assembly includes a second or distal end that extends distal of tip when the valve assembly is in the closed condition and an outer shell includes one or more windows to view a colored band or end portion indicator, which becomes exposed as the inner housing moves into the extended, open position, to determine when the valve assembly is in an actuated or open condition. The second end extends distal of tip when the valve assembly is in the closed condition to prevent the tip from being contaminated.

In a still further embodiment, the valve assembly includes a peel away seal (e.g., peel away tamper foil) adhered to a distal end to further prevent the tip of the valve assembly from being contaminated.

In an additional embodiment, the valve assembly may include a disinfectant media disposed on and/or around the tip within inner housing. Through movement of the valve assembly components, connection of Luer assembly, and/or other means, the disinfectant media disinfects the tip, further preventing the tip from being contaminated.

In a further embodiment, the valve assembly is a Luer slip valve assembly (e.g., for quick connection/access) and is integrated with a syringe.

In one or more implementations of the above embodiments, a press fit is created between the tip of a sealing pin and a distal end opening of a boss to seal the fluid passage and close the fluid path. In one implementation, the sealing surfaces have a taper. When the tip of the sealing pin engages the distal end opening, the distal end opening is deformed to create a high-pressure seal (i.e., press fit). This press fit is important for creating a liquid-tight seal in the valve assembly.

In one or more implementations of the above embodiments, the valve assemblies allow for 1) a disconnected and closed condition, 2) a connected and closed condition, and 3) a connected and open condition.

Other aspects and features of the present invention will become apparent from consideration of the following description taken in conjunction with the accompanying drawings.

DESCRIPTION OF THE PREFERRED EMBODIMENT

Certain embodiments as disclosed herein provide for a valve apparatus and method for controlling fluid flow through fluid line from a syringe or other fluid supply to a patient or a line connected to a patient. Although embodiments of valves, connecting devices, and assemblies are described herein with respect to medical connections, such valves, connecting devices, and assemblies are not limited to medical connections alone but may be applicable to any connection device or assembly that could benefit from the use of a rotational actuation force, status indicators, and/or any of the other features described herein.

After reading this description it will become apparent to one skilled in the art how to implement the invention in various alternative embodiments and alternative applications. However, although various embodiments of the present invention will be described herein, it is understood that these embodiments are presented by way of example only, and not limitation.

Figure 4:
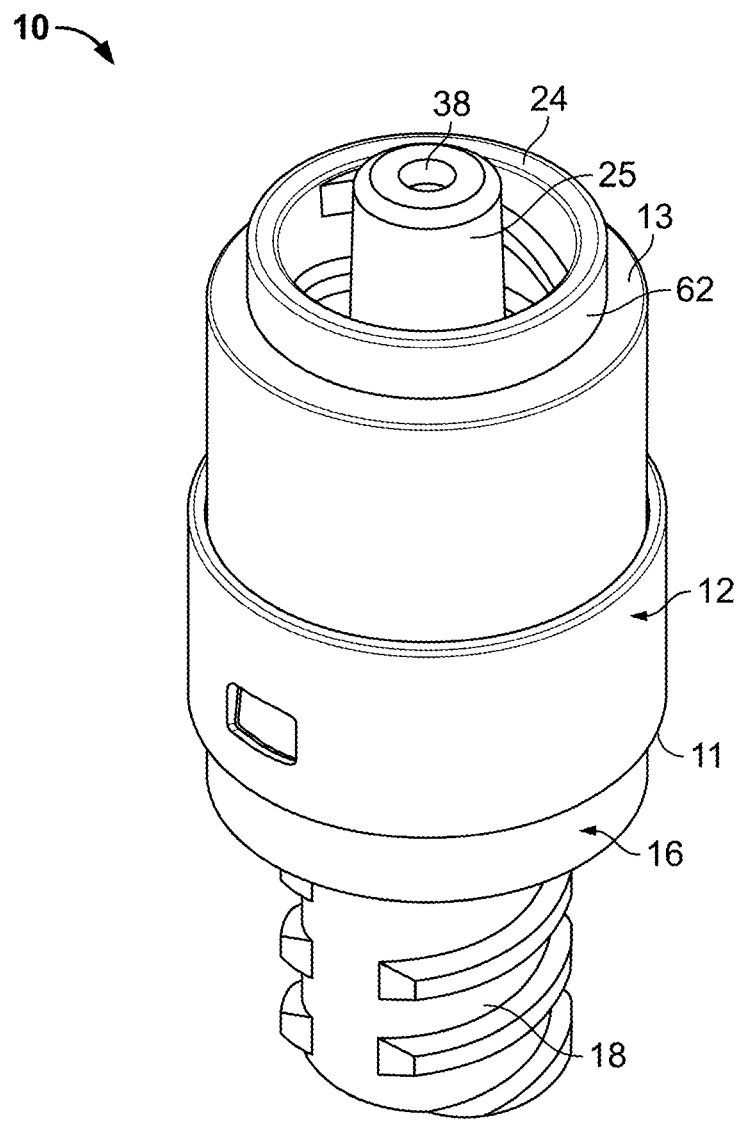
FIG. 4 is a perspective view similar to FIG. 1, with the valve in an open condition.
Figure 5:
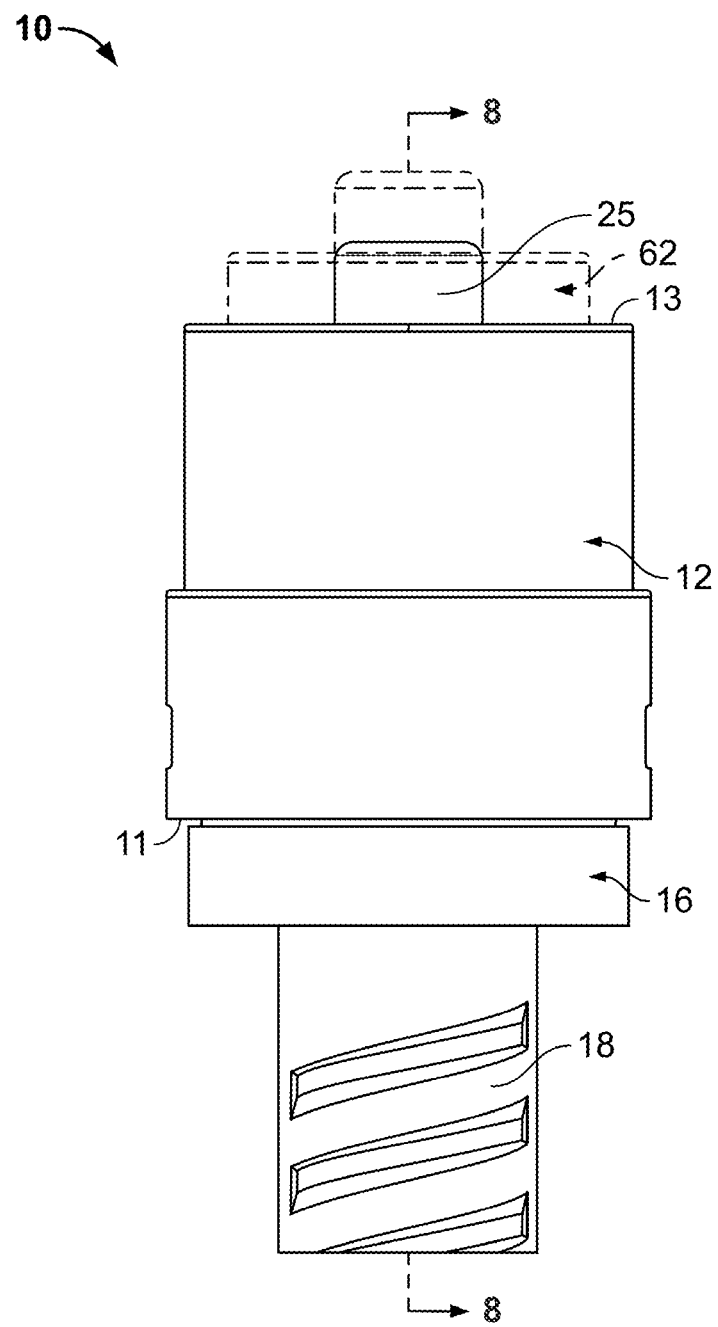
FIG. 5 is a side elevation view of the valve assembly of FIGS. 1 to 4, with the open condition shown in dotted outline.
Figure 6:
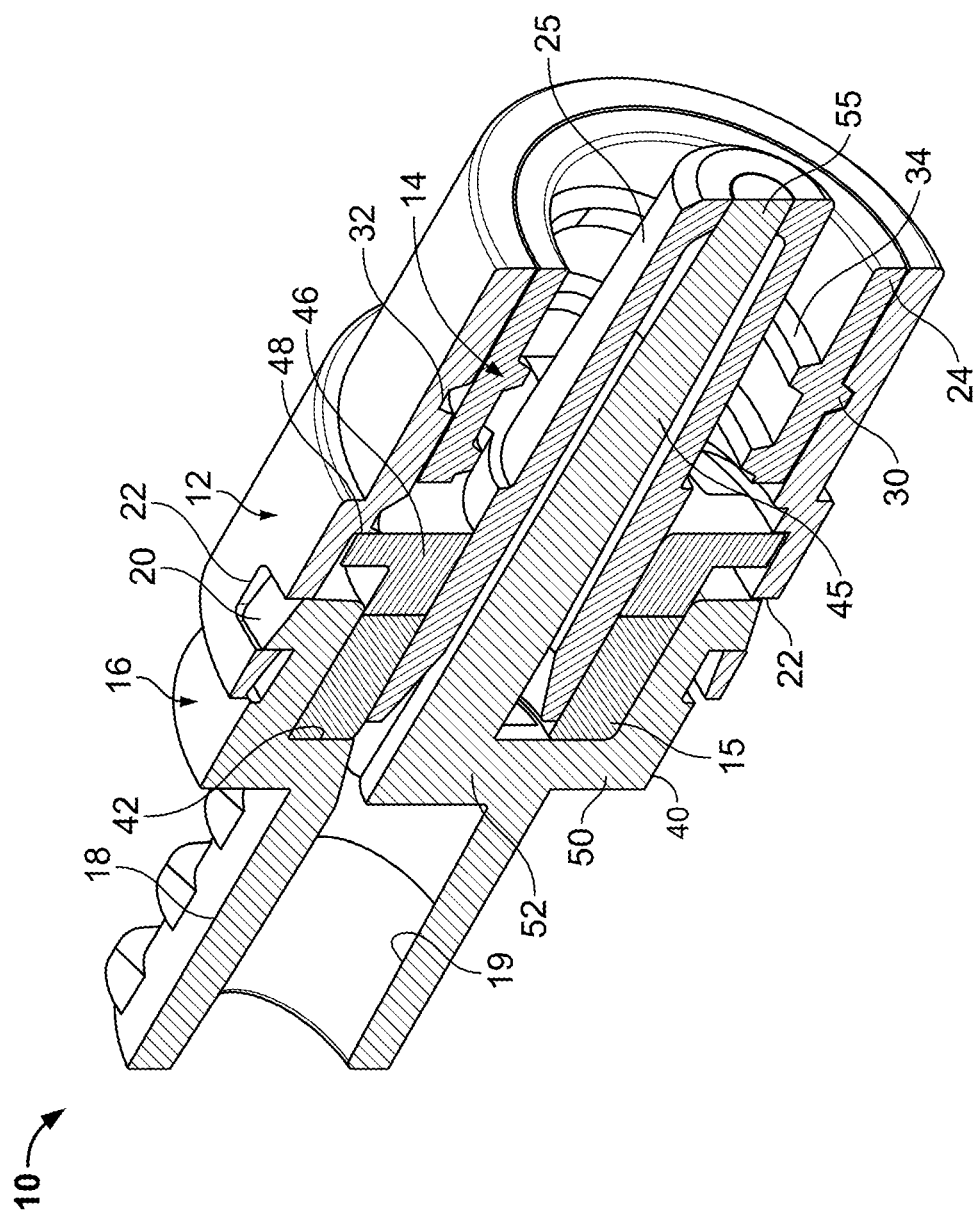
FIG. 6 is a cut away perspective view of the valve assembly in the closed condition of FIG. 1.
Figure 7:
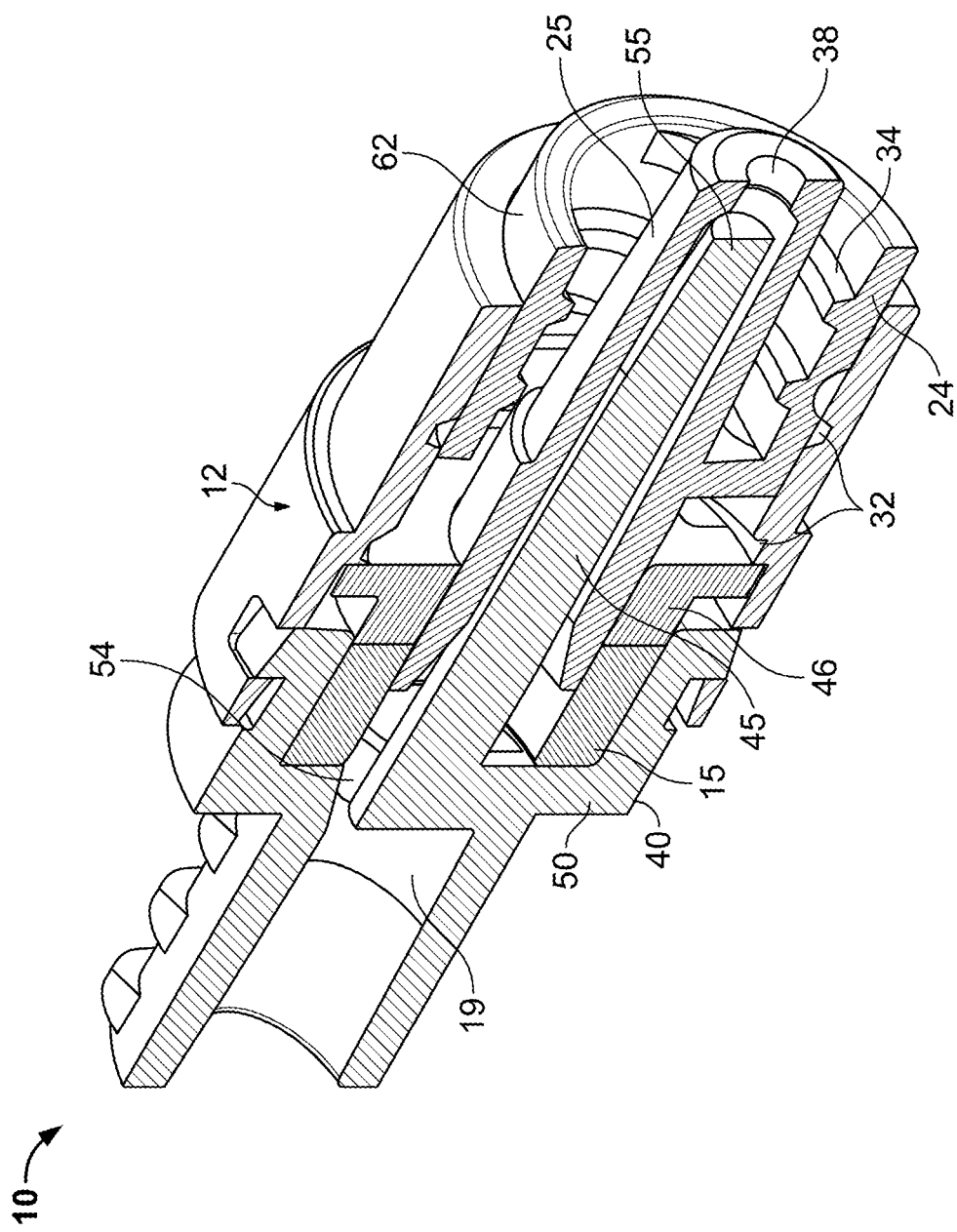
FIG. 7 is a cut away perspective view of the valve assembly in the open condition of FIG. 1.
Figure 8:
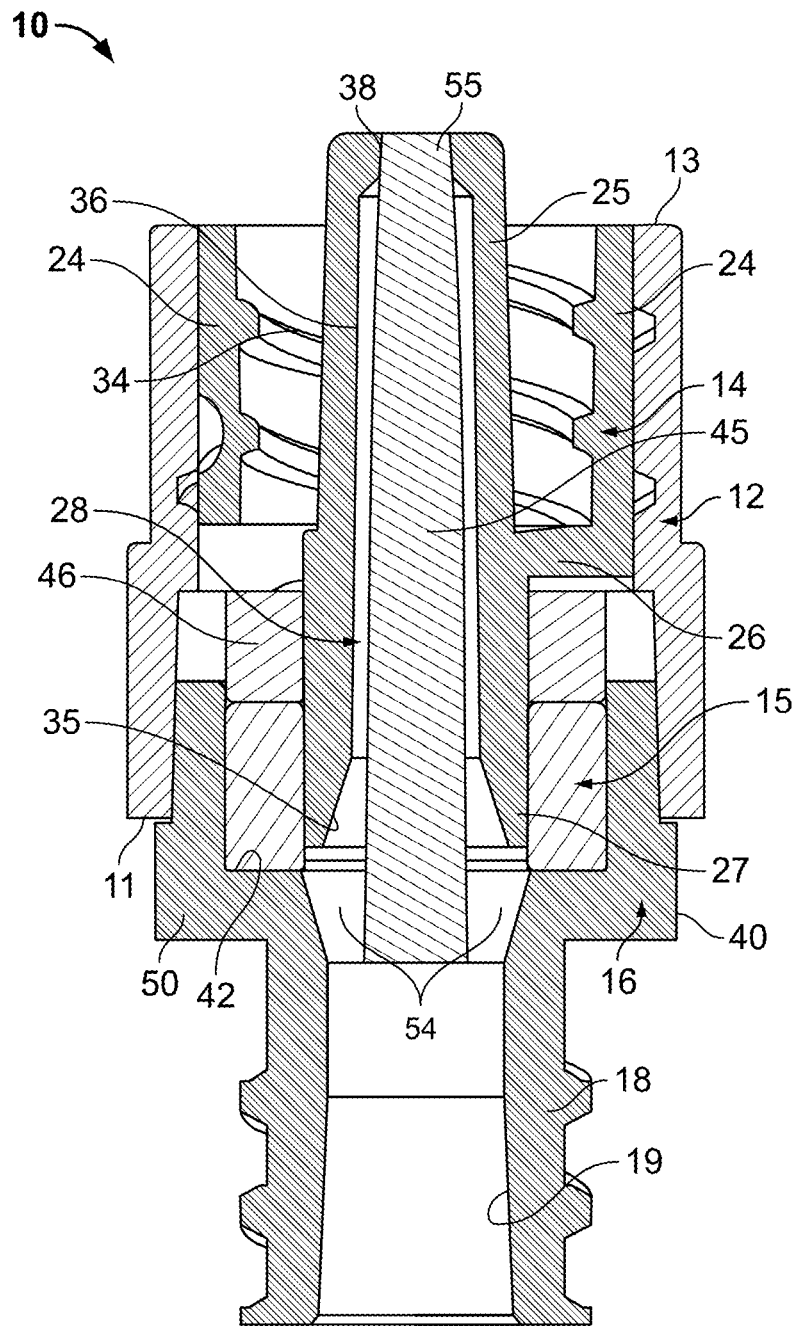
FIG. 8 is a cross-sectional view of the valve assembly in the closed condition, on the lines 8-8 of FIG. 5.

FIGS. 1 to 8 illustrate an embodiment of a stand-alone valve assembly 10 configured for delivering fluid in a fluid line from a syringe, IV, or a length of tubing, to a patient downstream of the valve assembly. As best illustrated in FIGS. 6 and 7, the assembly basically comprises an outer shell 12, an inner housing 14, a sealing member 15, and a backing member 16. The outer shell 12 has a through bore, a first or proximal end 11, and a second or distal end 13. The backing member 16 is secured in the proximal end 11 of outer shell 12 and includes a proximal connector 18 that extends axially away from the outer shell. Through bore 19 extends through backing member 16 to define part of the fluid path through the valve assembly, as best illustrated in FIG. 8. In one embodiment, proximal connector 18 is a threaded hub similar to a female Luer fitting. Outer shell 12 has a first end coupled to the backing member 16 via diametrically opposed tabs 20 on the outer surface of member 16 which are in snap engagement with corresponding openings 22 in the outer shell.

As best illustrated in FIGS. 6 and 8, inner housing 14 has an outer cylindrical sleeve or connector portion 24 movably secured in a distal end portion of outer sleeve 12, and a central tubular boss 25 which extends through sleeve 24. Boss 25 is secured to the sleeve via a two or more integral connecting portions or webs 26 and has a proximal end 27 received in the backing member 16, as described in more detail below. A through bore or fluid passageway 28 through boss 25 communicates with the through bore 19 in backing member 16, as illustrated in FIG. 8. Outer sleeve 24 has cam features such as outer camming threads 30 which engage inner cam features or camming threads 32 in the outer shell 12, as best illustrated in FIGS. 6 to 9, and an inner Luer thread 34 which surrounds boss 24 similar to a male Luer fitting. In one embodiment, the Luer thread 34 defines a first helical axis and the camming threads 32 on the inner housing define a second helical axis opposite the first helical axis. As illustrated in FIG. 8, through bore or passage 28 has a tapered inner or proximal end portion 35, a generally cylindrical bore portion 36 which extends along the majority of the length of passage 19, and a smaller diameter outlet end opening 38 which may be of tapering or uniform diameter.

Backing member 16 has an enlarged base portion 40 with a recessed seat 42 in which annular seal member 15 is seated, and a sealing pin 45 extends from base portion 40 through the seat and seal member and into the passageway 28 through boss 25 in the inner housing. Seal member 15 is retained in base portion 40 via retaining ring 46 which abuts against a shoulder or rim 48 in outer shell 12, as illustrated in FIGS. 6 and 7. Boss 25 slides through ring 46 and is in sealed, sliding engagement with annular seal member 15 as the inner housing moves between the closed, sealed condition and the open condition. Sealing pin 45 may be formed integrally with backing member 16, as illustrated in FIGS. 6 to 9, or may be formed separately and secured to the backing member in alternative embodiments. In this embodiment, the rear or inner end of sealing pin 45 is secured to backing member 16 at the intersection or shoulder 50 between enlarged base portion 40 and proximal connector 18, via integral webs or connecting portions 52 (FIG. 3), leaving openings 54 between connecting portions 52 to allow fluid communication between passageway or bore 19 proximal connector 18 and the through bore or passageway 28 through inner housing 14.

Figure 1:
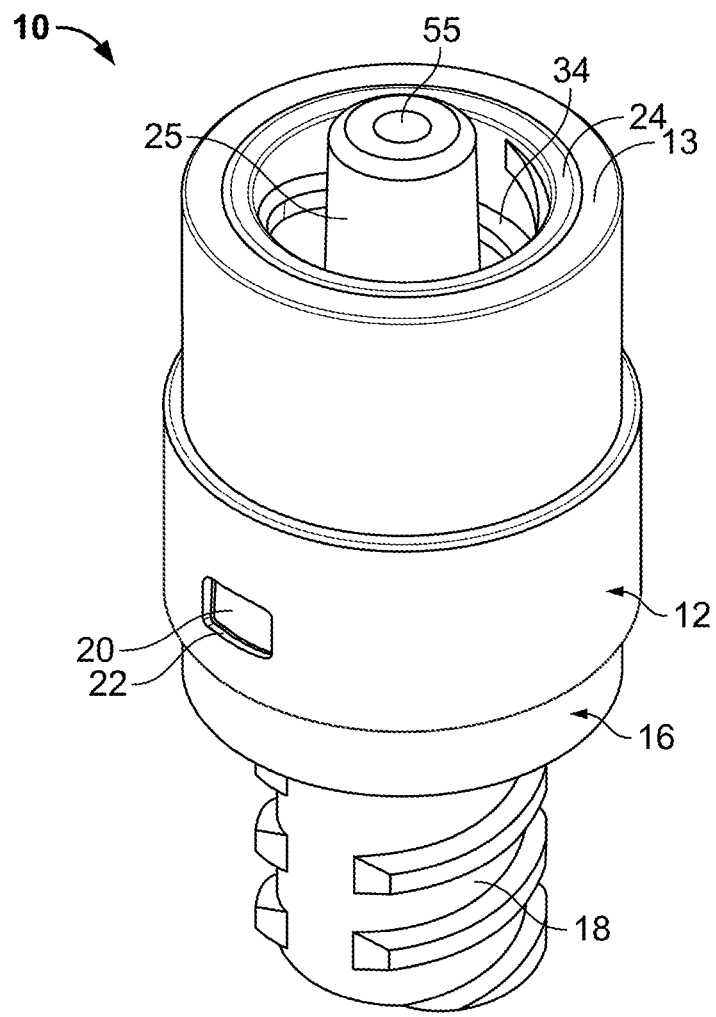
FIG. 1 is a perspective view of one embodiment of a valve assembly for controlling fluid flow, with the valve in a closed condition.
Figure 2:
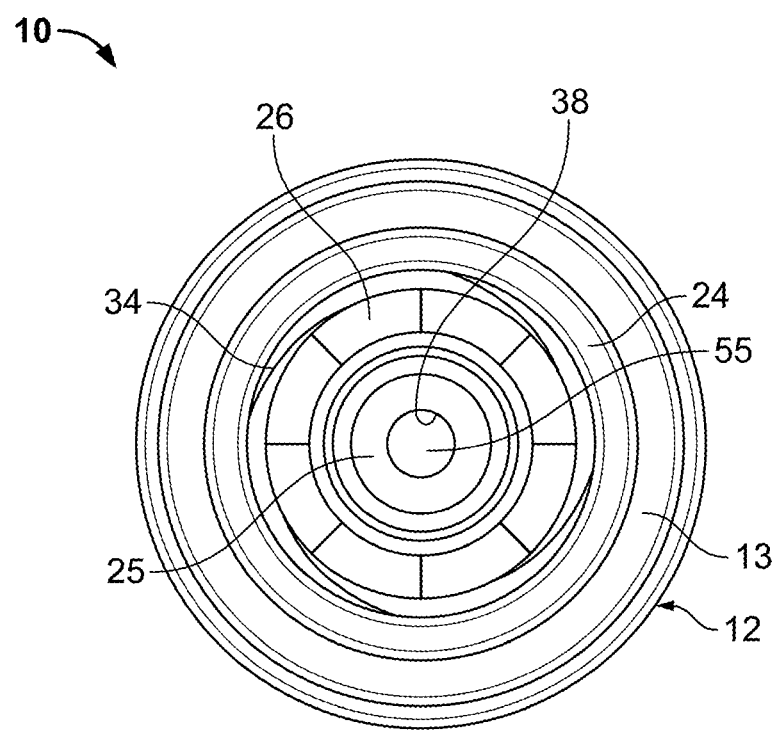
FIG. 2 is a top plan view of the valve assembly of FIG. 1.
Figure 3:
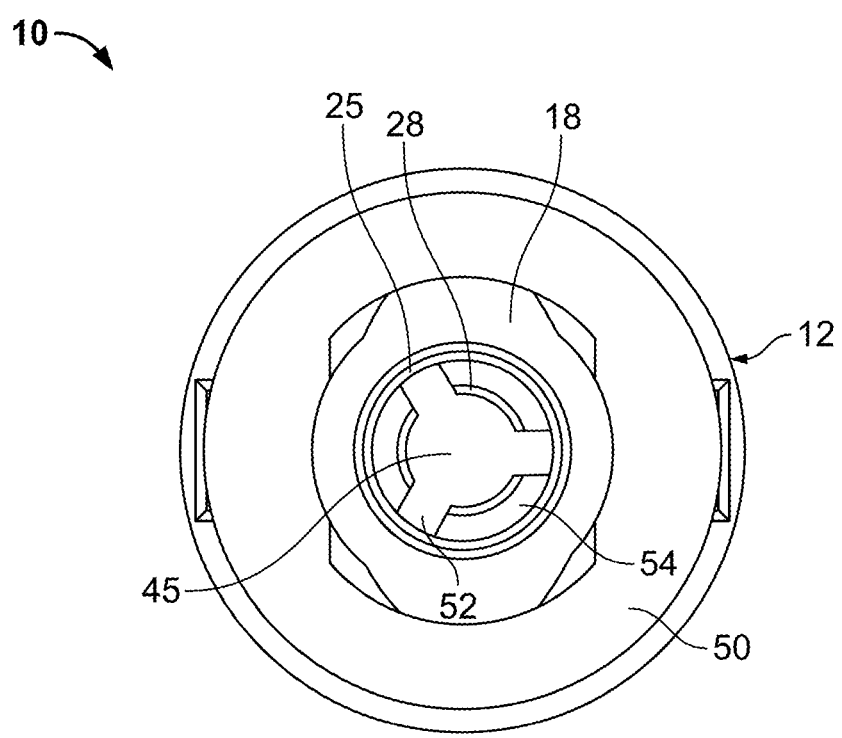
FIG. 3 is a bottom plan view of the valve assembly of FIG. 1.

FIGS. 1, 5 (solid line), 6 and 8 illustrate the assembly in a closed, sealed condition. In the illustrated embodiment, sealing pin 45 is a solid member and has a tapered distal tip 55 which is in sealing engagement with the reduced diameter distal end portion or opening 38 of through bore 28 in boss 25, as illustrated in FIGS. 6 and 8. In this condition, an annular passageway is still present between the enlarged cylindrical portion 36 of the boss through bore and the opposing surface of the pin, but the exit or distal end opening 38 is sealed by the mating, sealed engagement between opposing portions of tapered distal tip 55 and opening 38. In one embodiment, opening 38 has a taper matching that of tip 55 or an inner diameter substantially matching the diameter of the distal tip, so that the fluid passage through the valve assembly is substantially sealed in the closed condition.

Figure 9:
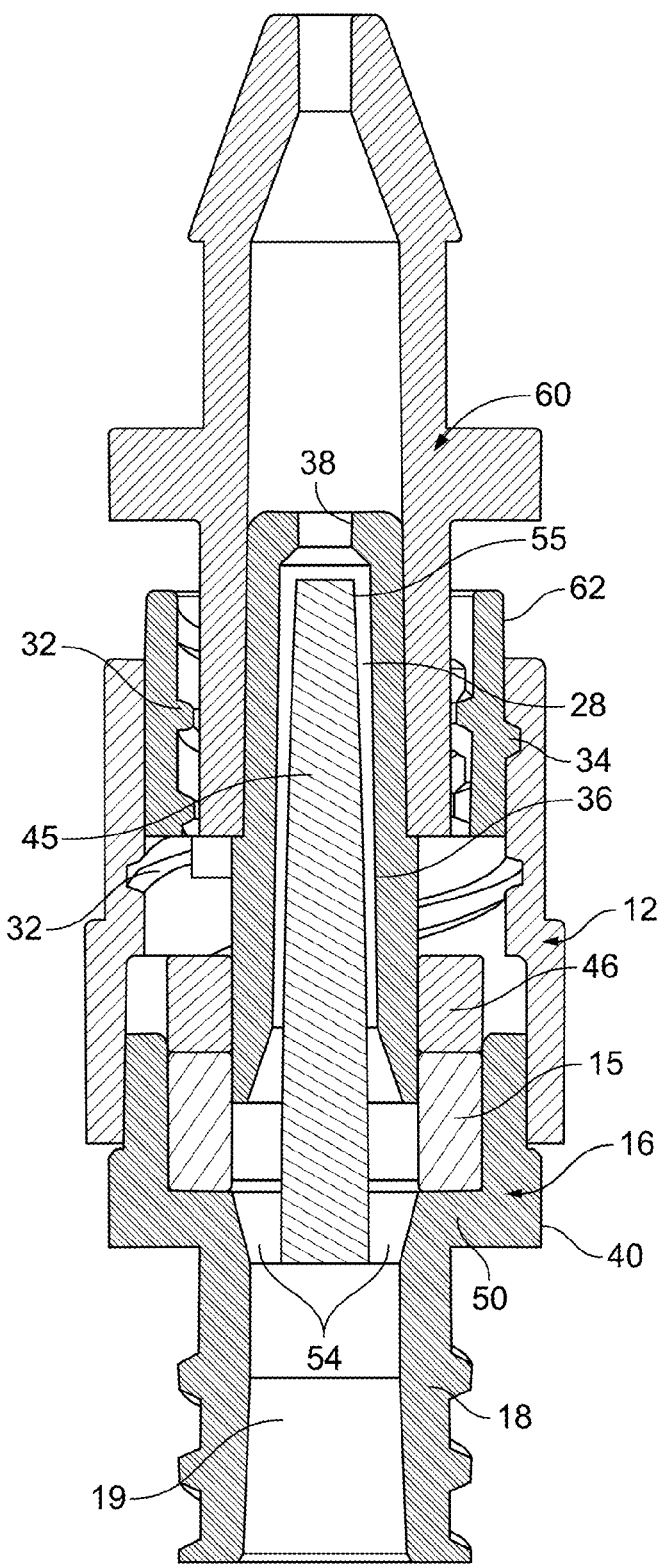
FIG. 9 is a cross-sectional view similar to FIG. 8 but showing the valve in the actuated or open condition after connection to a male Luer fitting.
Figure 10:
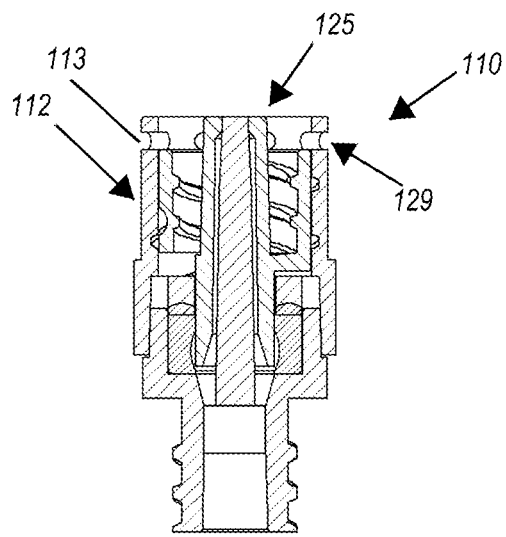
FIG. 10 is a cross-sectional view of another embodiment of a valve assembly in a closed condition.

FIGS. 4, 5 (dotted outline), 7 and 9 illustrate the assembly in an open condition. When it is desired to deliver fluid via a fluid line, a connector of the fluid line, e.g., a syringe or other container, tubing, and the like (not shown) may be threaded into the proximal connector of the backing member. Thereafter, a female Luer fitting, such as fitting 60 illustrated in FIG. 9, is threaded into the second end 13 of the inner housing 14, thereby slidably engaging the connector threads 34 with outer threads on the connector. Initially, the frictional resistance of the inner housing 14 to movement may allow the connector to slidably thread into the connector threads 34 without substantial movement of the inner housing 14. However, once the resistance of the connector to further threading increases or when the connector bottoms out in the connector threads 34, the continued rotation of the connector causes the inner housing 14 to rotate. This rotation causes the camming features or threads 30, 32 on the outer surface of inner housing sleeve 24 and the inner surface of outer shell 12, respectively, to engage one another to direct the inner housing 14 helically in a direction away from the base portion 40 of the backing member, so that the distal end of the boss also moves away from the tip 55 of the sealing pin. This moves the inner housing rotationally and distally from the closed position to the open position of FIGS. 7 and 9. In the open position, the distal end opening 38 of the boss is spaced from the tip 55 of the sealing pin, to complete the fluid passageway through the annular portion 28 around the end of tip 55 and out through the distal end opening 38 into the Luer fitting 60.

Thus, in the closed position, the tip of the sealing pin 45 is received in the tapered distal end opening 38 in boss 25 to substantially seal or close the fluid path, as shown in FIGS. 6 and 8, while in the open position, the inner housing 14 is moved distally and helically, such that the tip is withdrawn from the tapered distal end opening 38, thereby opening the annular passage around the sealing pin 45. In the illustrated open condition, the fluid path extends from the bore 19 in proximal connector 18, through the openings 54 in backing member 16 and the annular passageway between the inner end of pin 45 and seal member 15, and into the tapered inlet portion 35 of the boss 25, before flowing through annular passageway 28, around the end of pin 45, and out of opening 38.

Optionally, at least a portion of the sealing pin 45, e.g., the tip 55, may be formed from material that may enhance the seal between the sealing pin 45 and the distal end opening 38 in inner housing 14. For example, the tip may be formed an elastomeric material, such as silicone, and the like, which may sufficiently contact the inner wall of the opening 38 without substantial adhesion that may otherwise resist opening the valve 10.

During use, the valve 10 may be initially provided as shown in FIGS. 6 and 8, i.e., with the inner housing 14 in the closed position, e.g., with the tapered fluid outlet opening 38 substantially sealed by the tip of the sealing pin. The user may feel only a single substantially continuous rotation as they thread the connector, e.g. connector 60 or other types of female Luer connectors, into the connector threads 34, while the inner housing may consequently exhibit two distinct actions substantially simultaneously or subsequently to one another, i.e., engagement of the connector threads 34 on the inner housing with mating threads on the connector, and helical movement of the inner housing from the closed position to the open position due to the engagement between camming threads 30 and 32. As the inner housing moves into the extended, open position of FIGS. 4, 7 and 9, an end portion 62 of the outer sleeve is exposed. This end portion may be suitably colored or provided with indicia to identify the fact that the valve is open. This provides a clear visual indication when the valve is open and closed, which is an important safety feature, i.e. if a colored band or end portion 62 of the sleeve (which may be red, for example) is exposed, the valve is open. If the colored band is concealed inside the outer shell, as in FIGS. 6 and 8, the valve is closed and a connector may be removed. The engagement of the camming threads to move the inner housing into the open position may also be accompanied by a clicking sound or the like when the inner end of connector 60 engages the web 26, to indicate movement into an open position.

After sufficient fluid is delivered or if it is otherwise desired to close the fluid path and/or disconnect the valve 10 from the fluid line, the connector 60 may be unthreaded from the second end of the inner housing, thereby directing the inner housing from the open position of FIGS. 7 and 9 to the closed position of FIGS. 6 and 8, such that the tip of the sealing pin 45 again engages in the distal end opening 38 of the boss 25 to substantially seal the fluid passage and close the fluid path. This action may create a slight vacuum within the valve 10, thereby drawing any excess fluid adjacent the distal end of the inner housing 14 into the valve rather than risking the fluid leaking from the valve. Such a "negative bolus" effect may be useful if the fluid is corrosive or toxic, e.g., to reduce exposure of the fluid to an operator of the valve 10 and/or a patient being treated with the fluid.

A press fit is created between the tip of the sealing pin 45 and the distal end opening 38 of the boss 25 to seal the fluid passage and close the fluid path. In an embodiment of the invention, the sealing surfaces (i.e., external surface of the tip of the sealing pin 45 and the inner surface of the distal end opening 38) have a six degree taper. When the tip of the sealing pin 45 engages the distal end opening 38, the distal end opening 38 is deformed to create a high-pressure seal (i.e., press fit). This press fit is important for creating a liquid-tight seal in the valve assembly.

The valve assembly described above includes only four main parts, specifically the outer shell, inner housing, backing member, and annular seal member, and is relatively easy and inexpensive to manufacture and assemble, and is very easy to use.

In alternative embodiments of valve or valve assembly 10, proximal end connector 18 may be replaced with alternative connector devices for connecting the valve in a fluid line, or permanently connecting the valve to an outlet end of a needleless syringe.

With reference to FIGS. 10-28, a variety of valve assemblies constructed in accordance with different embodiments of the invention will be described. Because the valve assemblies of FIGS. 10-28 are generally similar the valve assembly 10 described above with respect to FIGS. 1-9, the description of the valve assembly 10 is incorporated herein and generally only features that are different from the valve assembly 10 will be described in turn below with respect to FIGS. 10-28.

Figure 11:
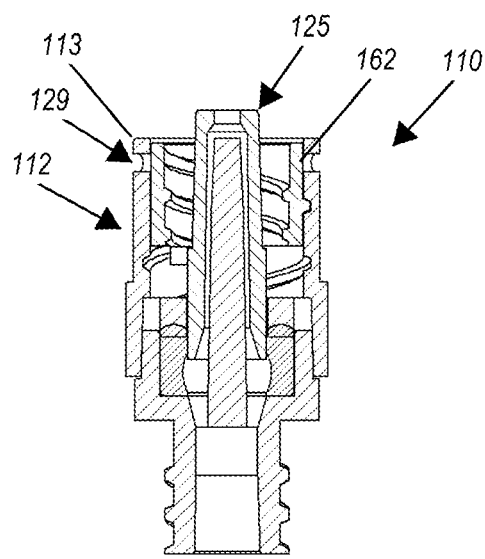
FIG. 11 is a cross-sectional view similar to FIG. 10 but showing the valve in the actuated or open condition.
Figure 12:
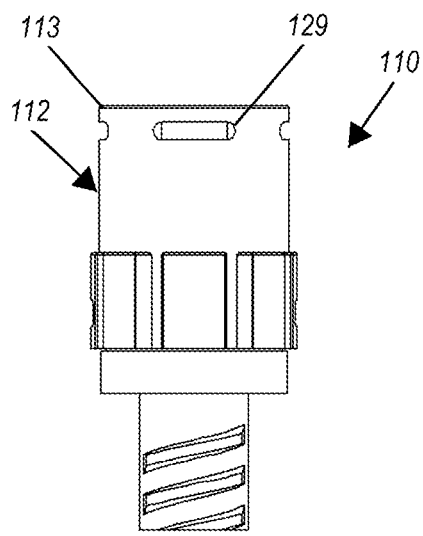
FIG. 12 is a front elevational view of the valve assembly in FIG. 10 in a closed condition.
Figure 13:
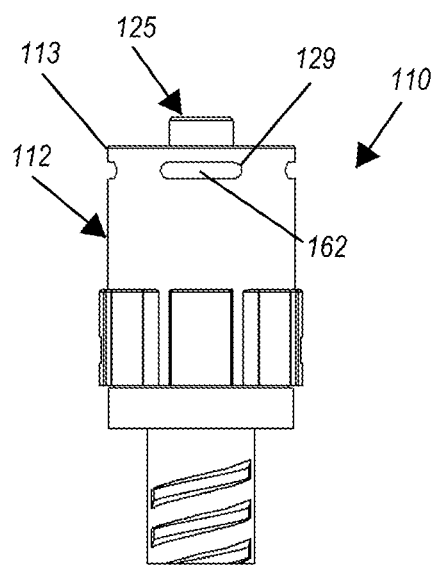
FIG. 13 is a front elevational view similar to FIG. 12 but showing the valve in the actuated or open condition.
Figure 14:
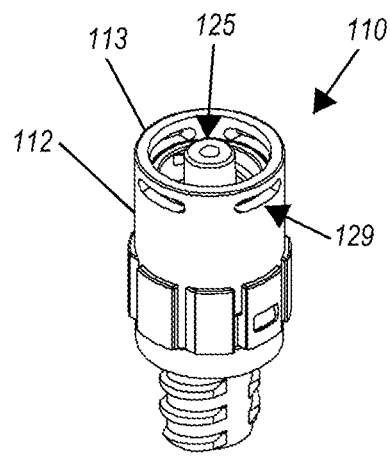
FIG. 14 is a perspective view of the valve assembly in FIG. 10 in a closed condition.
Figure 15:
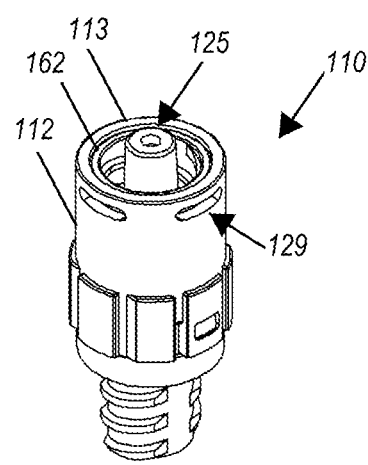
FIG. 15 is a perspective view similar to FIG. 12 but showing the valve in the actuated or open condition.
Figure 16:
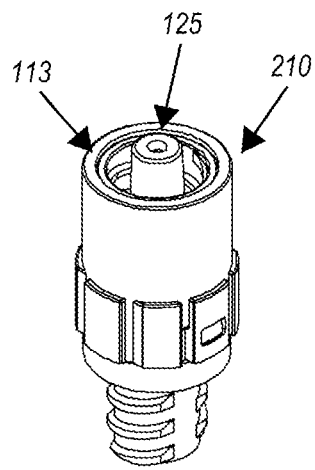
FIG. 16 is a perspective view of an additional embodiment of a valve assembly in a closed condition.
Figure 17:
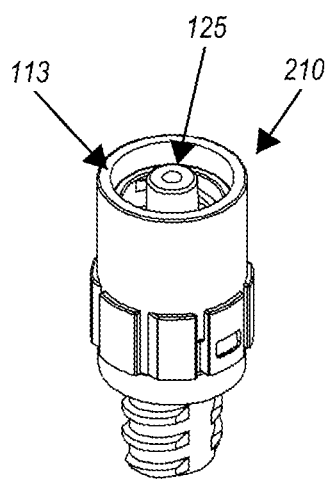
FIG. 17 is a perspective view similar to FIG. 16 but showing the valve in the closed condition.
Figure 18:
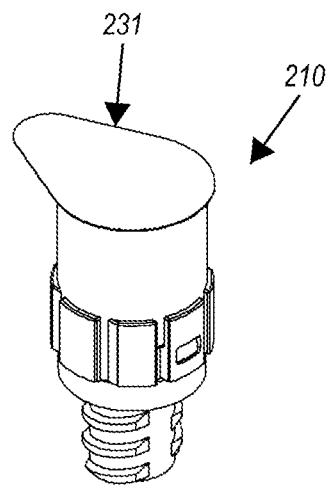
FIG. 18 is a perspective view of a further embodiment of a valve assembly including a peel away seal.
Figure 19:
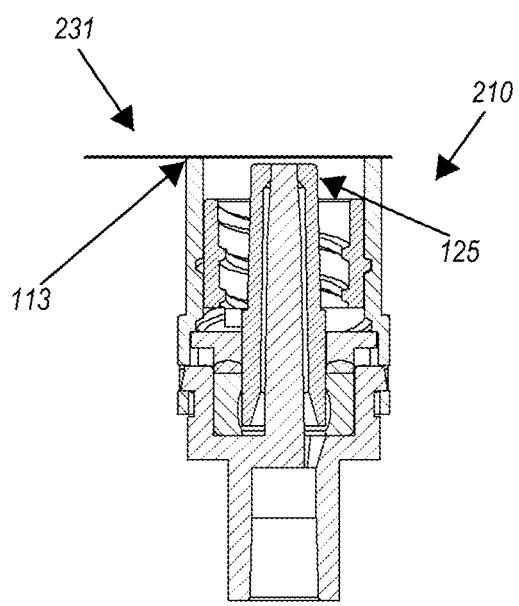
FIG. 19 is a cross-sectional view of the valve assembly in FIG. 18 and shows the valve in the closed condition.
Figure 20:
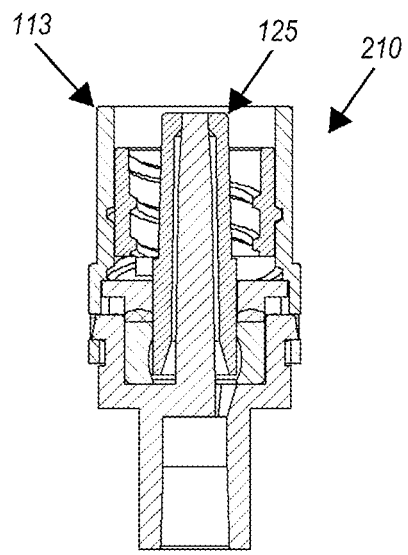
FIG. 20 is a cross-sectional view of the valve assembly in FIG. 18 and shows the peel away seal removed and the valve in the closed condition.
Figure 21:
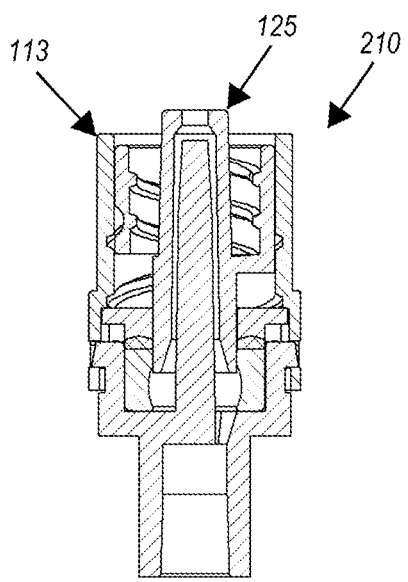
FIG. 21 is a cross-sectional view similar to FIG. 20 but showing the valve in the actuated or open condition.

FIGS. 10-15 illustrate another embodiment of a safety male Luer valve assembly 110 that is similar to the valve assembly 10 except that the outer shell 112 of the valve assembly 110 includes second or distal end 113 which covers the end portion 162 of the inner housing in the extended, open position of FIG. 11. Tip 125 of the barrel is below distal end 113 of outer shell 112 when valve assembly is open as in FIG. 11, and flush with distal end 113 when valve assembly is closed, as in FIG. 10. Outer shell 112 includes one or more windows (e.g., 2 windows, 3 windows, 4 windows, 5 windows, etc.) 129 in distal end portion 113 to view colored band or end portion indicator 162, which becomes exposed (FIGS. 11, 13, 15) as the inner housing moves into the extended, open position, to determine when the valve assembly 110 is in an actuated or open condition. Second end 113 extending distal of tip 125 when the valve assembly 110 is in the closed condition prevents tip 125 from being contaminated (e.g., prevents tip 125 from contacting a contaminated surface/object). Preventing the tip 125 from being contaminated, prevents the valve assembly 110, IV line, etc. from being contaminated. In one or more embodiments of the valve assembly 110, the safety male Luer valve assembly 110 may be pre-attached to an IV line.

FIGS. 16-21 illustrate an additional embodiment of a safety male Luer valve assembly 210 that is similar to the valve assembly 110 described above with respect to FIGS. 10-15 except that the valve assembly 210 includes a peel away seal (e.g., peel away tamper foil) 231 adhered to distal end 113 (see FIGS. 18 to 20) and does not include window(s) 129. The same reference numbers are used for parts in valve assembly 210 which are equivalent to parts in valve assembly 110 of the previous embodiment. The peel away seal 231 further prevents the tip 125 of the valve assembly 210 from being contaminated (e.g., prevents tip 125 from contacting a contaminated surface/object) when the valve assembly 110 is in the closed condition prior to use. Preventing the tip 125 from being contaminated, prevents the valve assembly 210, IV line, etc. from being contaminated. When the safety male Luer valve assembly 210 is ready to be connected to a female Luer connector, the peel away seal 231 is peeled away/removed from the distal end 113 and disposed of. The safety male Luer valve assembly 210 is then connected to the female Luer connector in the manner described above with respect to FIGS. 1-9. FIGS. 16, 17, 20, and 21 may represent perspective views and cross-sectional views of the valve assembly 210 with the peel away seal 231 removed or may represent another embodiment that is similar to the valve assembly 110 described above with respect to FIGS. 10-15 except that the valve assembly 210 does not include window(s) 129.

In a further embodiment of the valve assemblies 10, 110, 210, the valve assemblies 10, 110, 210 may include a disinfectant media (e.g., foam, closed cell foam, open cell foam, cotton) saturated with a disinfectant such as, but not limited to isopropyl alcohol. The disinfectant media is disposed on and/or around tip 25, 125, within inner housing 14. Through movement of the valve assemblies components, connection of Luer assembly, and/or other means, the disinfectant media disinfects the tip 25, 125, further preventing the tip 25, 125 from being contaminated. Preventing the tip 125 from being contaminated, prevents the valve assembly 110, IV line, etc. from being contaminated.

The valve assemblies 10, 110, 210 shown with respect to FIGS. 16-21 and described above are Luer lock valve assemblies. The principles of the invention shown and described herein may also be applied to Luer slip valve assemblies. Accordingly, with reference to FIGS. 22-28, a still further embodiment of a valve assembly 310, which is a Luer slip valve assembly (e.g., for quick connection/access), will be described. As in the previous embodiments, the valve assembly 310 comprises an outer housing or shell 316, an inner housing 315, and a backing member 318. Backing member 318 in this embodiment has a portion which extends out of the proximal end of outer housing 316 and is integrated with the outer housing of a syringe 333. Backing member 318 has a base 319 and a sealing pin 320 projecting from base through a bore in inner housing 315, as in previous embodiments. However, in this embodiment, base 319 is disposed near a distal end of outer shell 316, instead of near a proximal end of the shell as in the previous embodiments, and inner housing 315 is slidably engaged over backing member 318 between the backing member and outer shell, rather than inside a seating recess in the backing member.

Figure 22:
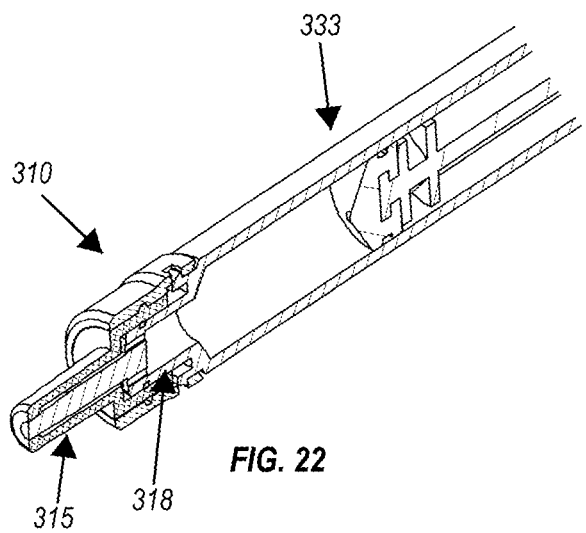
FIG. 22 is a partial perspective and cross-sectional view of a still further embodiment of a valve assembly shown integrated with a syringe and the valve in the closed condition.
Figure 23:
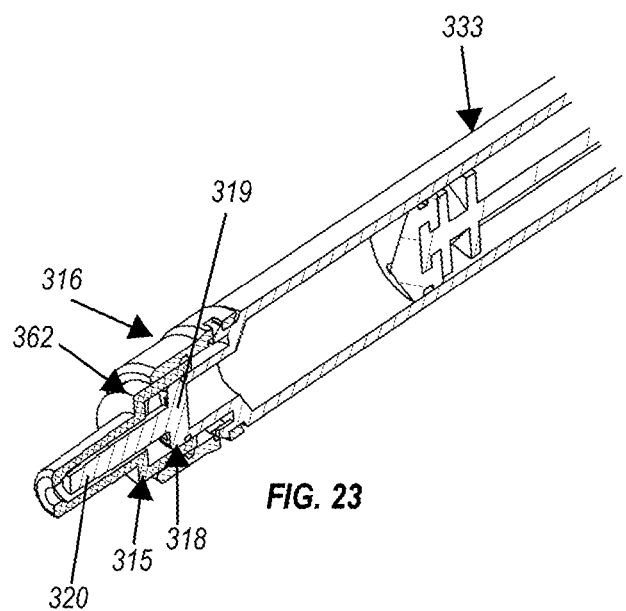
FIG. 23 is a partial perspective and cross-sectional view similar to FIG. 22 but showing the valve in the actuated or open condition.
Figure 24:
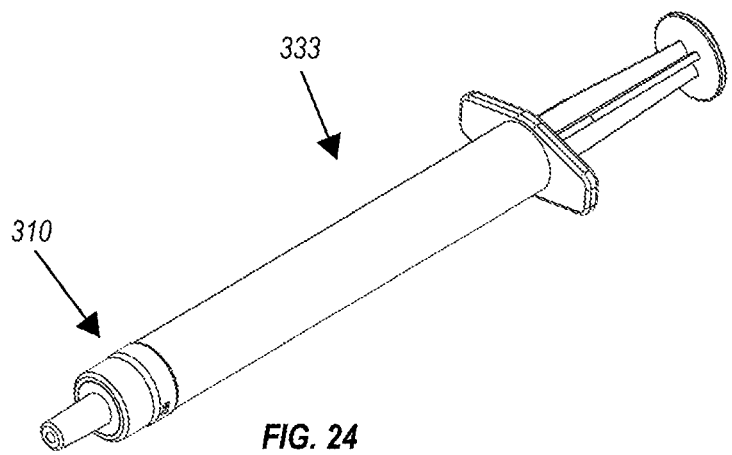
FIG. 24 is a perspective view of the valve assembly and syringe of FIG. 22 and the valve in the closed condition.
Figure 25:
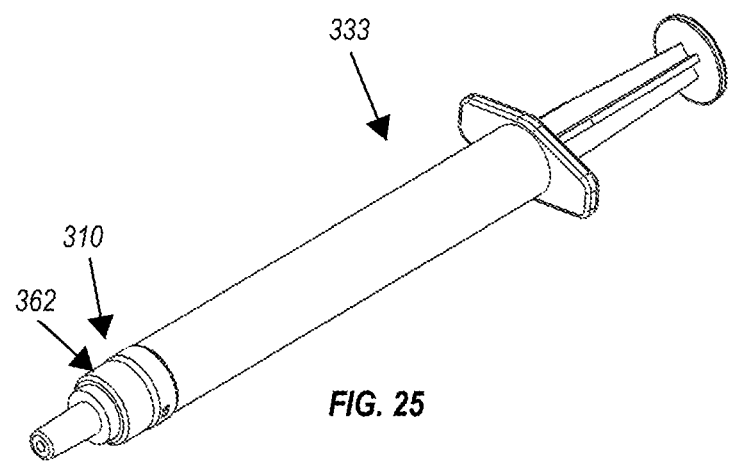
FIG. 25 is a perspective view similar to FIG. 24 but showing the valve in the actuated or open condition.
Figure 26:
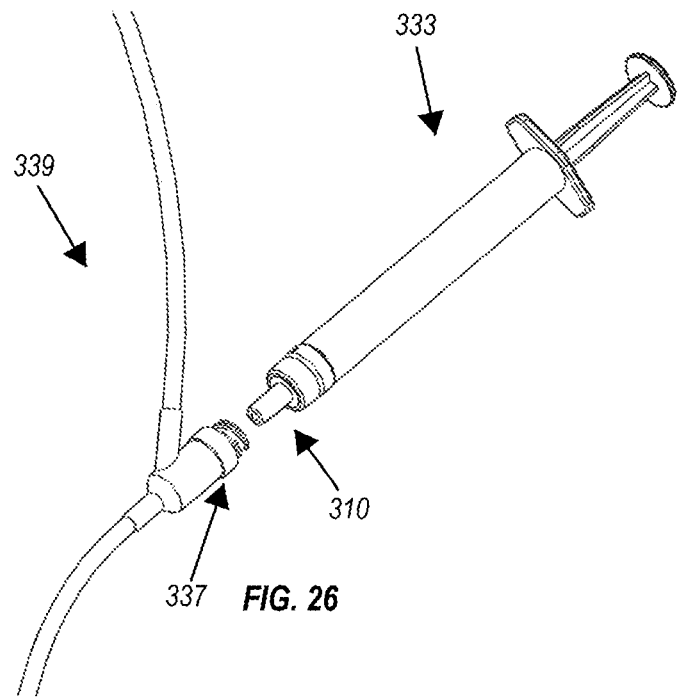
FIG. 26 is a perspective view of the valve assembly and syringe of FIG. 24 shown just prior to connection to a female Luer connector of an IV line.
Figure 27:
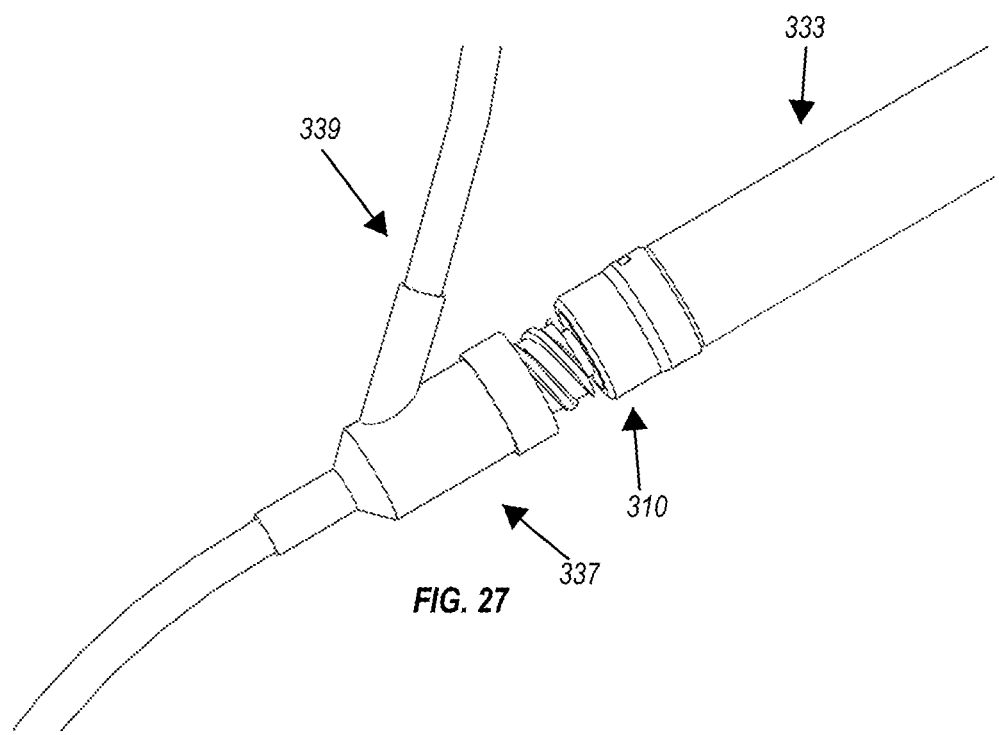
FIG. 27 is a perspective view of the valve assembly and syringe of FIG. 24 being applied/connected to the female Luer connector of FIG. 26 with the valve still in the closed condition.
Figure 28:
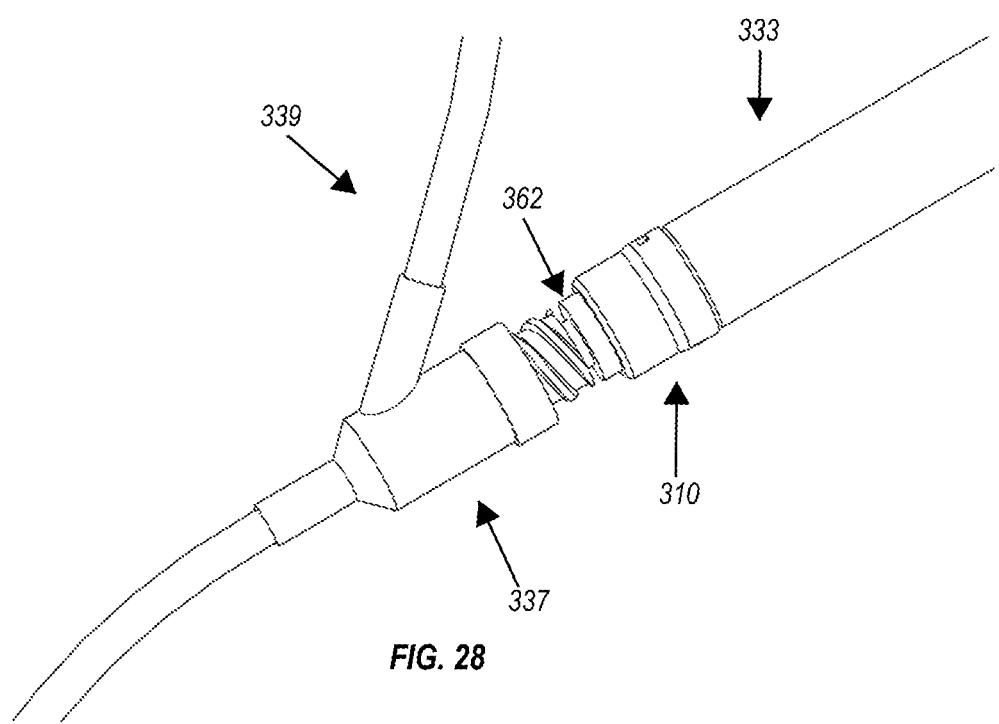
FIG. 28 is a perspective view of the valve assembly and syringe of FIG. 24 connected to the female Luer connector of FIG. 26 with the valve in the actuated or open condition.

The Luer slip valve assembly 310 is otherwise similar to the valve assemblies 10, 110, 210. FIGS. 22 and 24 show the Luer slip valve assembly 310 in the closed condition. FIGS. 23 and 25 show the Luer slip valve assembly 310 in the actuated or open condition. In the actuated or open condition, colored band or end portion indicator 362 is exposed as the inner housing moves into the extended, open position. The exposed, visible indicator 362 confirms to the user that the valve assembly 310 is in an actuated or open condition. FIG. 26 shows the valve assembly 310 and syringe 333 just prior to connection to a female Luer connector 337 of an IV line 339. FIG. 27 shows the valve assembly 310 and syringe 333 being applied/connected to the female Luer connector 337 with the valve assembly 310 in the closed condition (indicator 362 not visible). FIG. 28 shows the valve assembly 310 and syringe 333 connected to the female Luer connector 337 with the valve assembly 310 in the actuated condition (indicator 362 visible). Although the valve assembly 310 has been described as integrated into the syringe 333, in an alternative embodiment, the valve assembly 310 is separate from the syringe 333 and the backing member is releasably securable to the syringe in a similar manner to that described above in connection with the previous embodiments.

The valve assemblies 10, 110, 210, 310 allow for 1) a disconnected and closed condition, 2) a connected and closed condition, and 3) a connected and open condition. Past Luer lock valve assemblies allowed for only 1) a disconnected and closed condition and 3) a connected and open condition. Thus, with past Luer lock valve assemblies, the user may not know at what point the fluid path is sufficiently opened or closed during connection and disconnection of the two connectors. The user only knows that the fluid path is closed (e.g., the two connectors are deactuated), when the two connectors are completely disengaged, or disconnected, and separated.

In contrast, with the valve assemblies 10, 110, 210, 310, the user always knows the connection status and fluid path status of the two connectors.

Figure 31A:
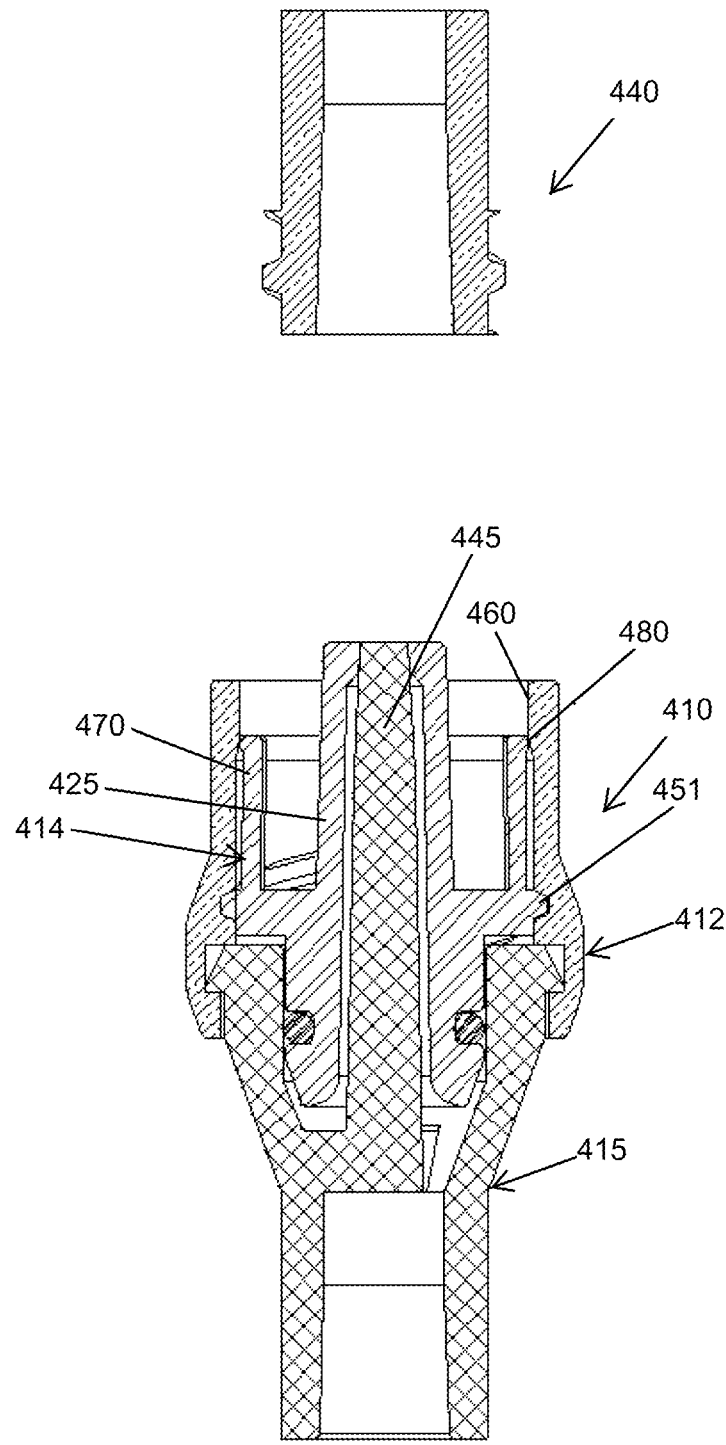
FIG. 31A is a cross-sectional view of the valve assembly of FIGS. 29A-29C and FIG. 30 on the line 31A-31A of FIG. 30, and shows the valve assembly in a closed condition and disconnected from a female Luer connector.
Figure 31B:
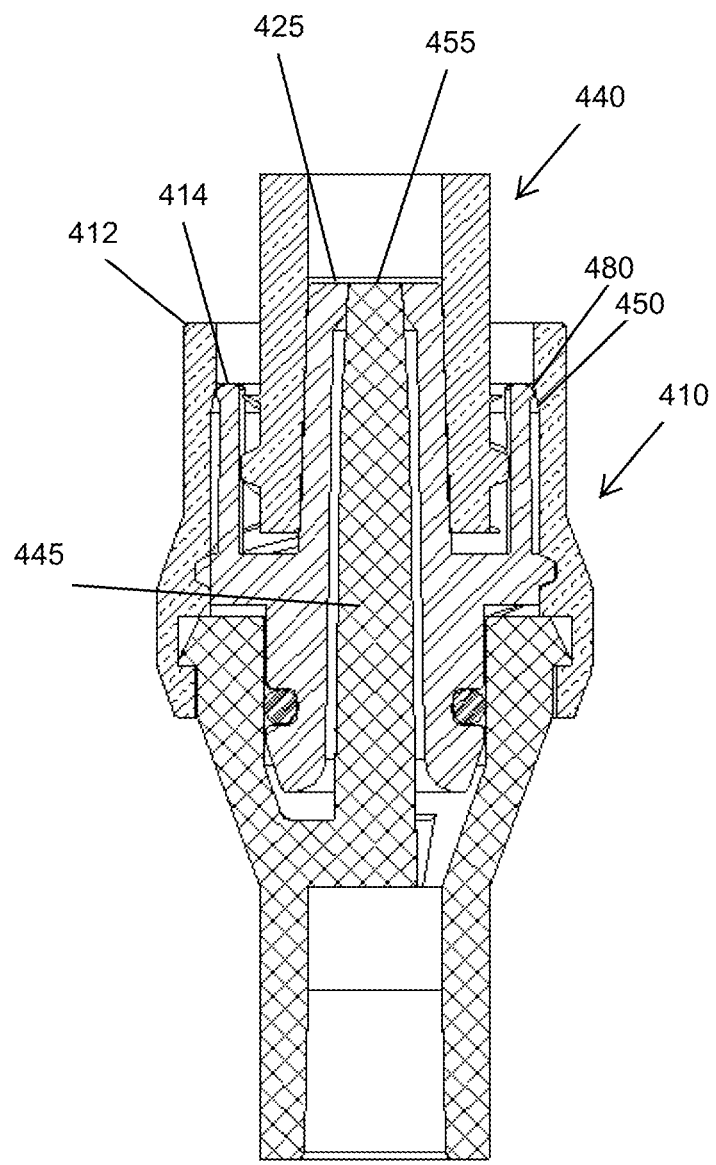
FIG. 31B is a cross-sectional view similar to FIG. 31A but showing the valve assembly in a closed condition and engaged with the female Luer connector.
Figure 31C:
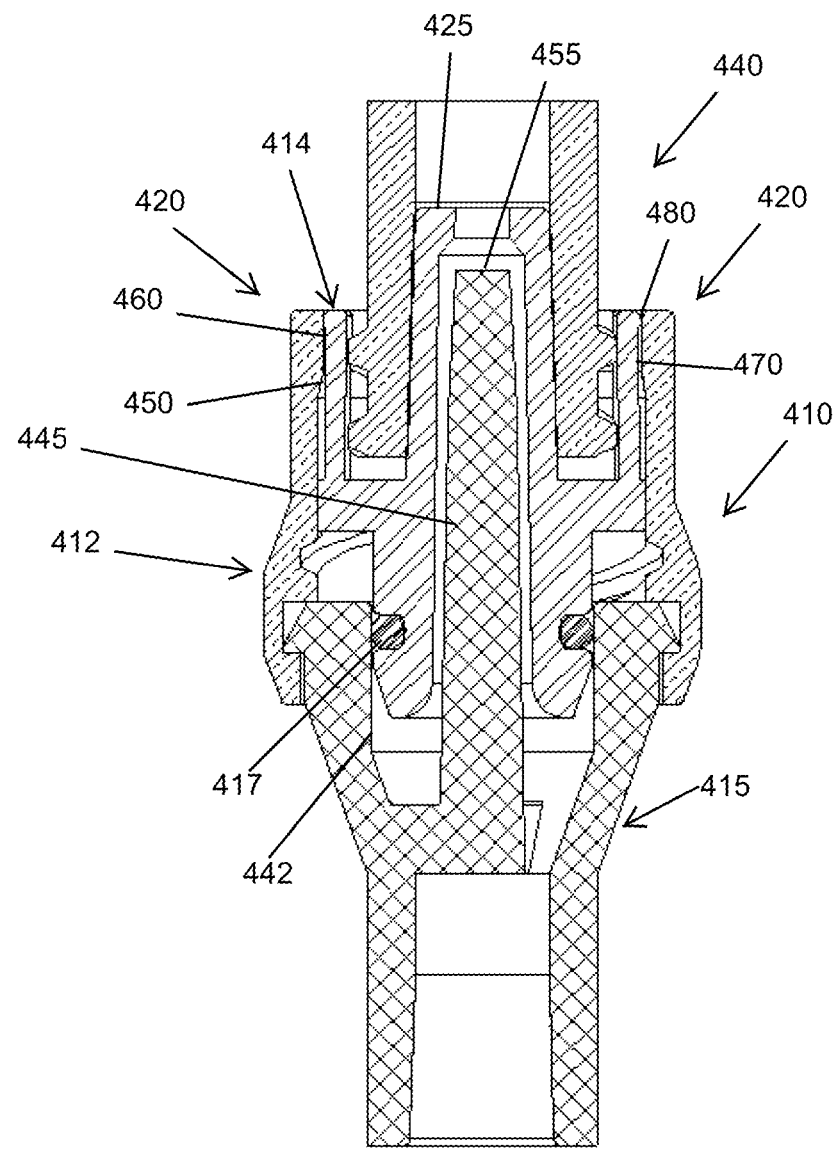
FIG. 31C is a cross-sectional view similar to FIGS. 31A and 31B, but showing the valve assembly in an open condition and connected with the female Luer connector.
Figure 32A:
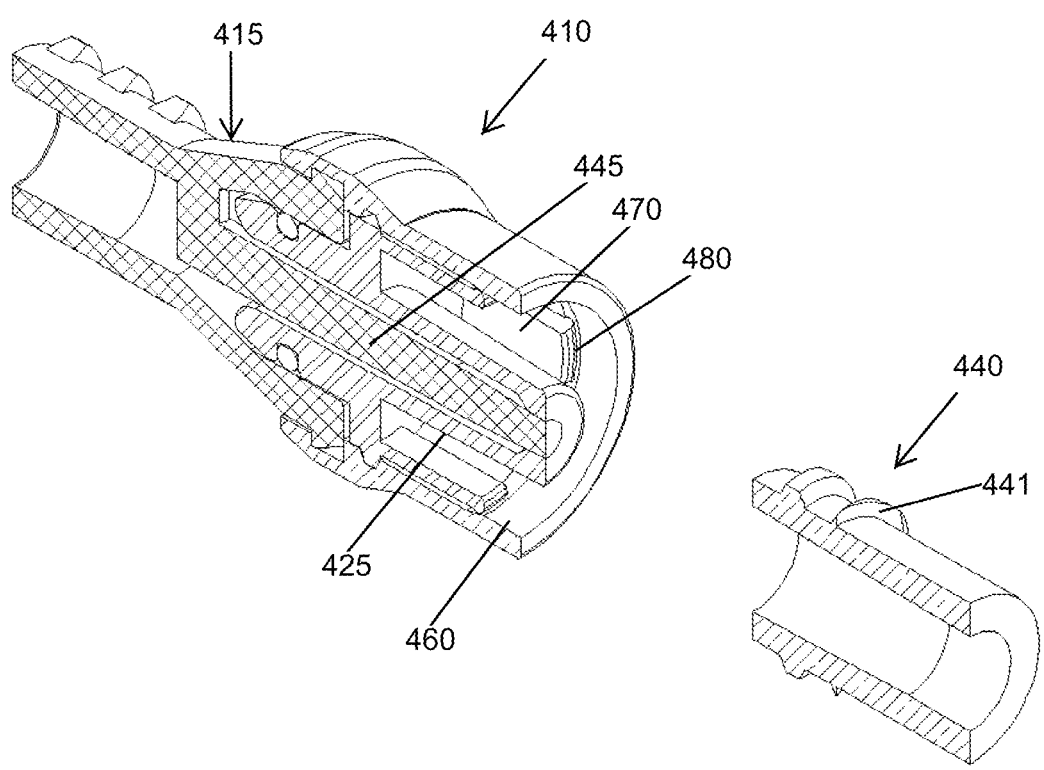
FIG. 32A is a partial perspective and cross-sectional view of the valve assembly of FIGS. 29A-29C in a closed condition and disconnected from a female Luer connector.
Figure 32B:
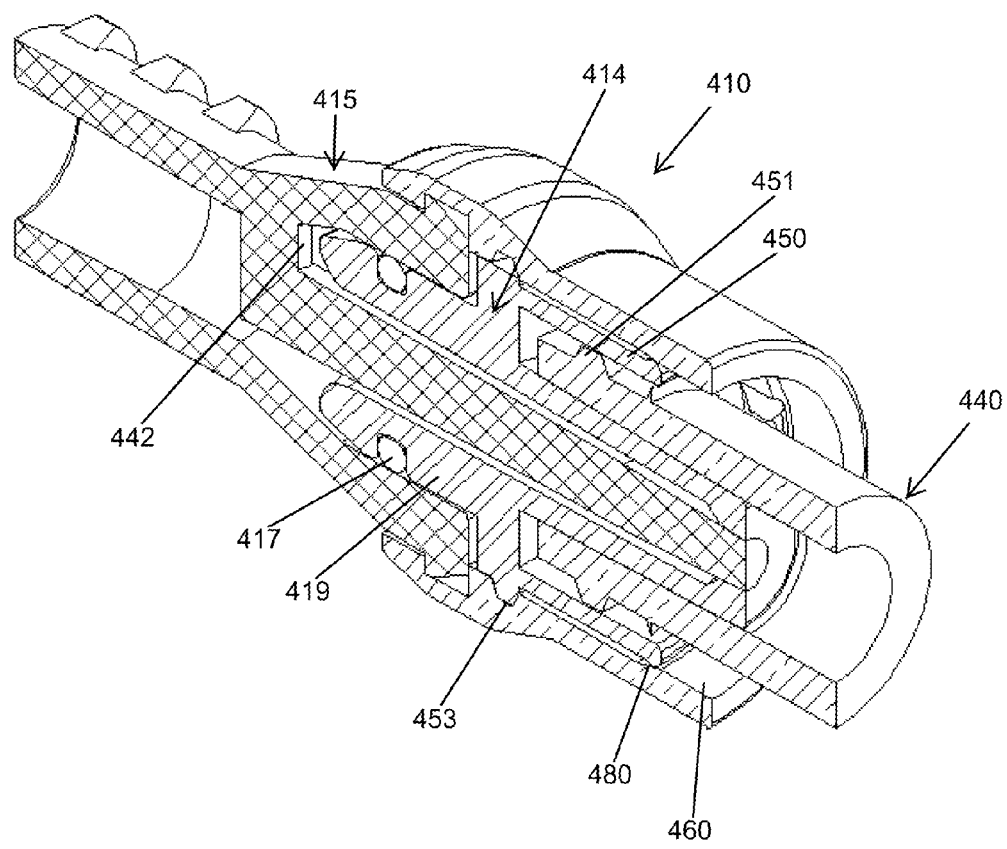
FIG. 32B is a partial perspective and cross-sectional view of the valve assembly of FIGS. 29A-29C in a closed condition and shown engaged with the female Luer connector.
Figure 32C:
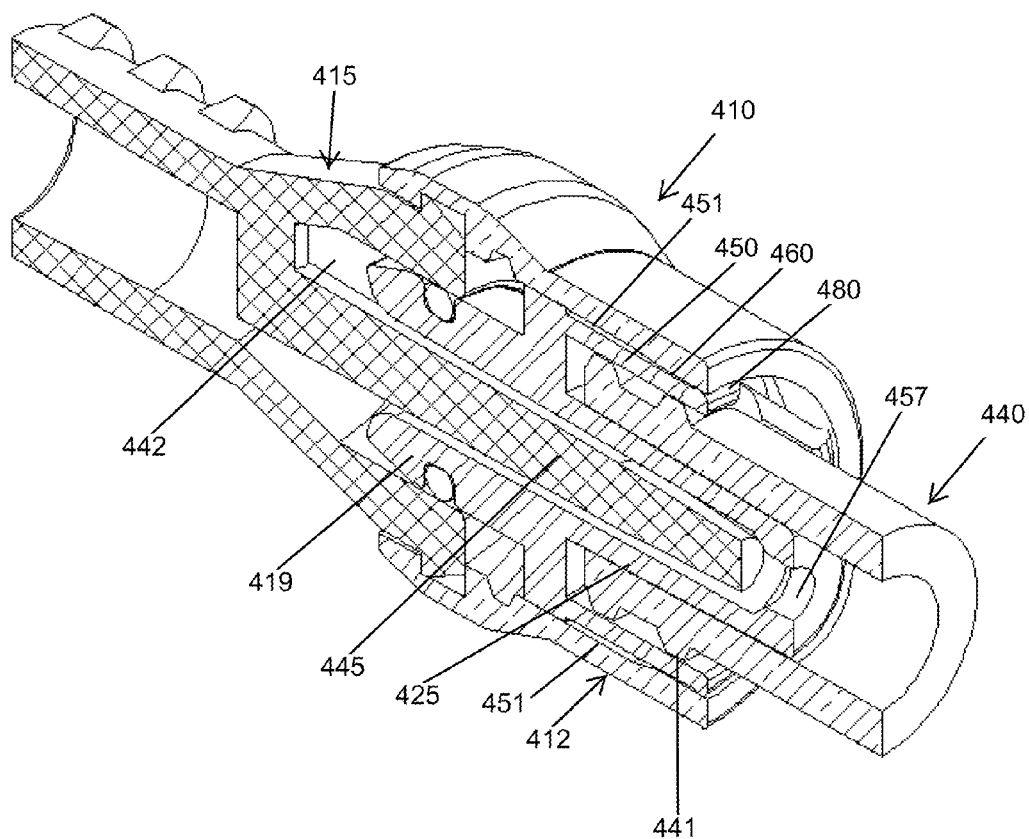
FIG. 32C is a partial perspective and cross-sectional view of the valve assembly of FIGS. 29A-29C in an open condition and shown engaged with the female Luer connector.

With reference to FIGS. 29A-32C, another embodiment of a safety male Luer valve assembly 410 will be described. The valve assembly 410 is similar to the valve assemblies 10, 110, 210, 310 described above. However, unlike the previous embodiments, the valve assembly 410 includes a hydraulic circuit securement mechanism or tamper proof mechanism 420 at a distal portion 430 of the valve assembly 410 that prevents female Luer connector 440 from disconnecting from the safety male Luer valve assembly 410 when the valve assembly 410 is in an open condition and engaged with the female Luer connector 440 as shown in FIGS. 29C, 31C, 32C.

Valve assembly 410 has an outer shell 412, an inner housing 414, and a backing or base member 415. As in the previous embodiments, the inner housing 414 is movably secured in a distal end portion of outer shell 412, and has an outer cylindrical hub or wall section 450 and a central tubular boss 425 which extends through hub 450. The proximal portion 419 of tubular boss 425 is slidably received in recessed seat 442 in base member 415, and a sealing member 417 such as an O-ring seal between tubular end portion 419 of the inner housing and recessed seat 442 is in sealing engagement with the inner wall surface of seat 442 (see FIG. 31A). Outer sleeve or hub 450 of inner housing 414 has camming threads 451 which engage inner cam features or threads 453 on outer shell 12, and an inner Luer thread similar to a male Luer fitting, designed for engagement with outer Luer threads 441 on a female Luer fitting or connector 440, as in the previous embodiments. Backing or base member 415 has a sealing pin 445 as in the previous embodiments which extends through the bore in tubular boss 425. Attachment to a matching Luer fitting causes the inner housing 414 to move relative to outer shell 412 and sealing pin 445 between a closed and sealed position as in FIGS. 31A and 32A, in which the end of pin 445 is in sealing engagement with the end opening 457 in the tubular boss 425, and an open or actuated position as illustrated in FIGS. 31C and 32C, in which the sealing pin 455 is spaced from opening 457. In this position, a passageway for fluid through the valve assembly is provided, in the same way as described above in connection with the first embodiment. When in the open position, the Luer fitting 440 cannot be removed, but must be rotated until the valve is again closed, into the intermediate position of FIGS. 31B and 32B, before it can be released.

This embodiment is similar to the embodiment of FIGS. 16 to 21 in that the end of inner housing or shell 414 does not extend from the distal end of outer shell 412 in the open or actuated position. Since this embodiment includes a securement mechanism to prevent or restrict female Luer connector 440 from disconnecting from the safety male Luer valve assembly 410 when the valve assembly 410 is in an open condition and engaged with the female Luer connector 440 as shown in FIGS. 29C, 31C, 32C, an indicator to show that the valve assembly is in the open condition is not needed.

The hydraulic circuit securement mechanism 420 will now be described in more detail. The through bore of outer shell 412 has an inner portion 451 of larger diameter and a distal end portion 460 of smaller diameter, with an inwardly angled interior wall section 450 connecting the larger and smaller diameter portions 451 and 460. Inner housing 414 includes four tines 470 terminating at distal ends in outwardly extending nubs 480.

Figure 29A:
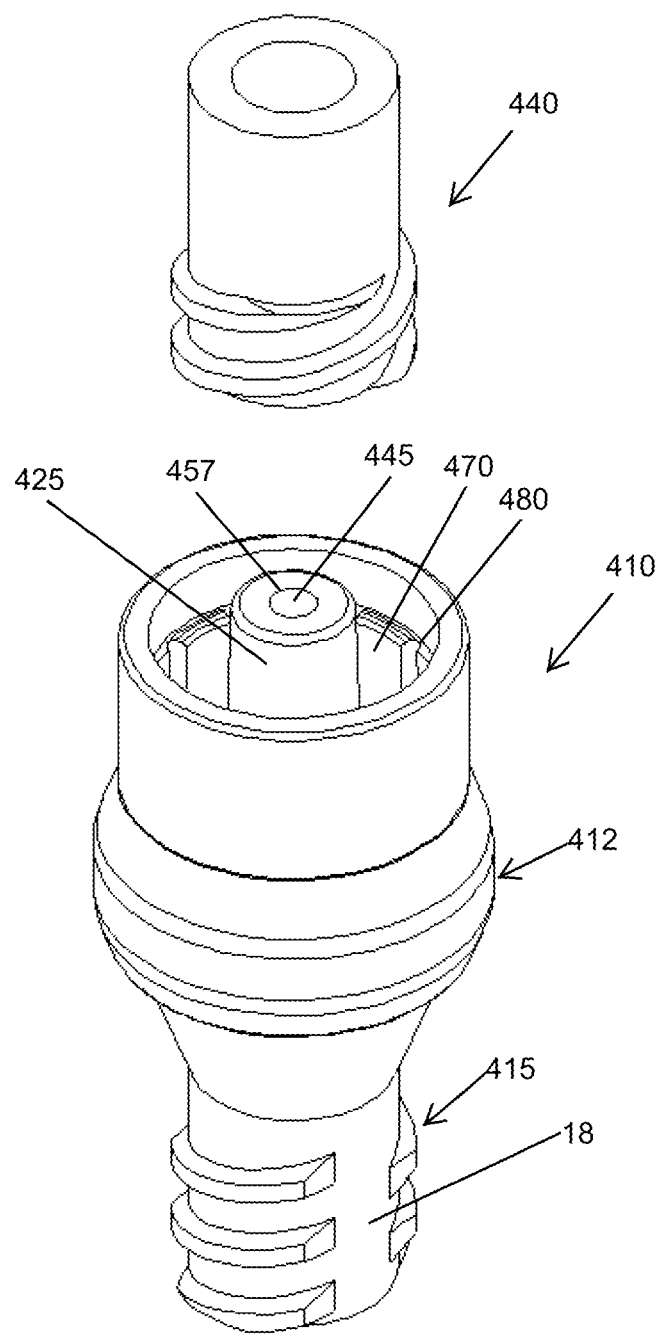
FIG. 29A is a perspective view of another embodiment of a valve assembly in a closed condition and disconnected from a female Luer connector.
Figure 29B:
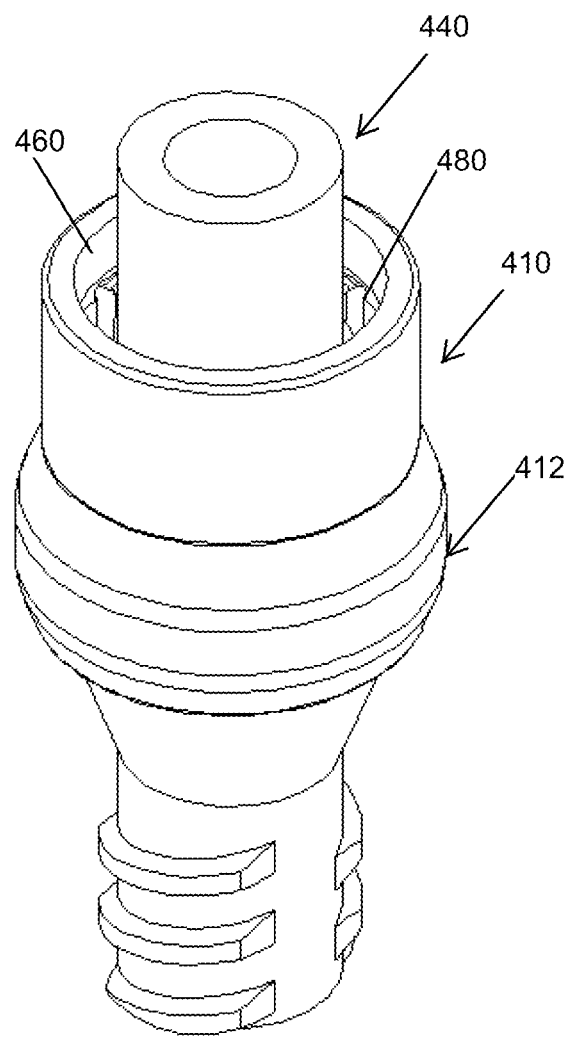
FIG. 29B is a perspective view of the valve assembly of FIG. 29A in a closed condition and shown engaged with the female Luer connector.
Figure 29C:
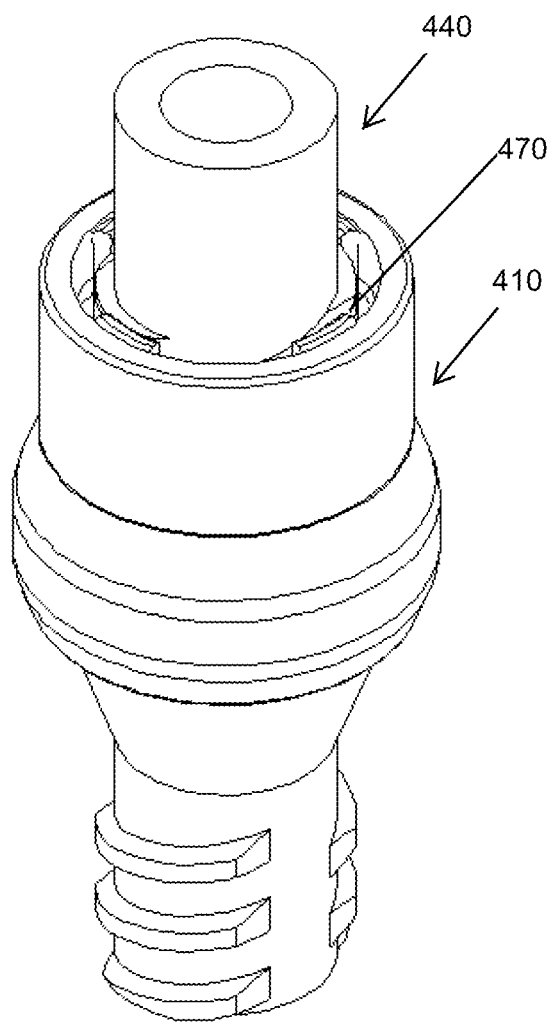
FIG. 29C is a perspective view of the valve assembly of FIG. 29A in an open condition and shown engaged with the female Luer connector.
Figure 30:
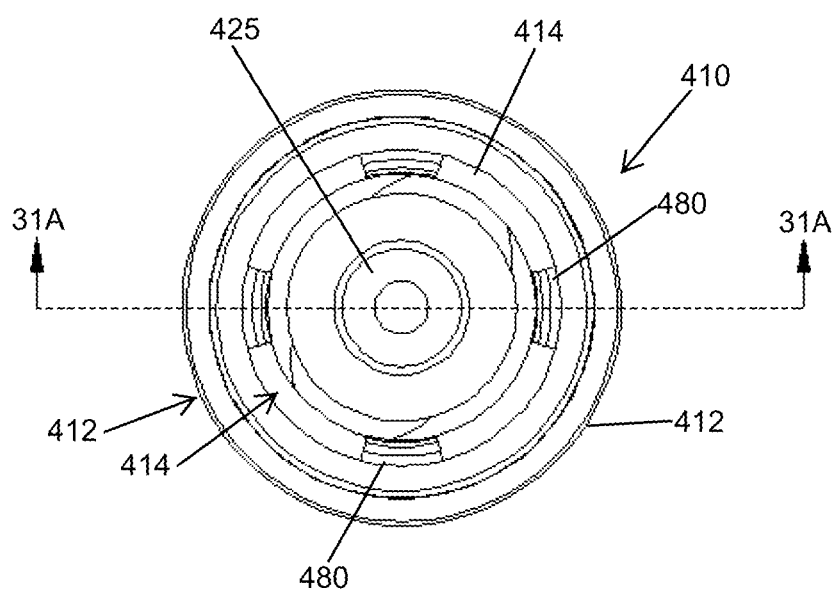
FIG. 30 is a top plan view of the valve assembly of FIGS. 29A-29C shown engaged with the female Luer connector.

With reference to FIGS. 29A-32C, the hydraulic circuit securement mechanism 420 will now be described in use. FIGS. 29A, 31A, and 32A show the safety male Luer valve assembly 410 in a closed condition and the female Luer connector 440 just prior to connection of the safety male Luer valve assembly 410 to the female Luer connector 440. FIGS. 29B, 31B, and 32B show the safety male Luer valve assembly 410 in a closed condition and the female Luer connector 440 rotatably engaged with the safety male Luer valve assembly 410. The female Luer connector 440 is rotatably connected to the safety male Luer valve assembly 410 in a manner similar to that described above and illustrated in FIGS. 4, 5, 7, and 9. When the female Luer connector 440 rotationally bottoms out in the inner housing 414, continued rotation of the female Luer connector 440 relative to the safety male Luer valve assembly 410 causes the inner housing 414 to rotate and move towards the distal end of the outer shell 412 of the safety male Luer valve assembly 410. As the inner housing 414 moves outward, the distal end of the boss 425 also moves away from the tip 455 of the sealing pin 445. This moves the inner housing rotationally and distally from the closed position shown in FIGS. 29B, 31B, and 32B to the open position shown in FIGS. 29C, 31C, and 32C. Simultaneously, with rotation of the female Luer connector 440 relative to the safety male Luer valve assembly 410, the outwardly extending nubs 480 of the tines 470 engage the inwardly angled interior wall section 450 and are forced inwardly to engage the smaller diameter interior wall section 460 of outer shell 420. This camming engagement process urges the enlarged ends of the tines 470 inwards to engage under the threads 441 of female Luer connector 440 as illustrated in FIGS. 31C and 32C, holding the connector in position relative to the inner housing 414, and preventing female Luer connector 440 from accidentally disconnecting from the safety male Luer valve assembly 410 when the valve assembly 410 is in an open condition and engaged with the female Luer connector 440.

When the connector 440 is to be disengaged, it is rotated in the opposite direction but is prevented from moving out of the valve assembly 410 until the inner housing 414 is retracted back to the position of FIG. 32B and the end of pin 445 is again in sealing engagement with the open end 457 of boss 425. At this point, the enlarged ends 480 of tines 470 are again engaged in the larger internal diameter portion 451 of outer shell 412, allowing the connector 440 to disconnect from the valve assembly.

Advantages of the valve assembly 410 include tamper proofing, extra safety, and quicker connect/disconnect between valve assembly 410 and female Luer connector 440. This is because the female Luer connector 440 does not have to be rotated as much with valve assembly 410 compared to prior Luer valve connection assemblies because the valve assembly 410 does not rely on outer threads of female Luer connector to secure female Luer connector to male Luer valve assembly.

Optionally, in any of the embodiments described above, one or more surfaces and/or components of the valves and/or connecting assemblies may be coated. The coating(s) may be applied to the desired surfaces by dipping, spraying, brushing, and the like.

For example, when needleless connectors are used to access intravenous catheters and tubing, it may be useful to protect the patients from contamination and growth of microorganisms at the point of entry into the catheter, as well as in the bloodstream. Blood stream infections ("BSI's") related to intravenous catheters are a substantial clinical and economic problem. They are associated with significant patient morbidity and mortality, and may lead to a substantial rise in hospital costs. Given that BSI's are considered preventable, as of Oct. 1, 2008, the major insurers, such as the US Centers for Medicare and Medicaid no longer reimburse for catheter related bloodstream infections. As such, it is desirable for the technologies adopted by hospitals to include built in mechanisms to protect against catheter related bloodstream infections.

Typically, short term catheters are colonized by skin microorganisms, as well as bacteria from the hub/lumen, the bloodstream, and infusate, in order of occurrence. Staphylococcus aureus and Staphylococcus epidermidis are the microorganisms most frequently involved in catheter related infections.

Two options for preventing catheter-related infections include the use of anti-adhesive biomaterials, and the incorporation of antimicrobial agents into the polymer material used for the connectors and/or catheters. The first option may serve two purposes, one being the prevention of non-specific bacterial adhesions, and the other being the adsorption of host components, which may promote bacterial adhesion.

For example, one approach involves the modification of biomaterial surfaces with hydrophilic coatings such as heparin and polyethylene oxide. These coatings are effective in reducing surface adhesions or biofouling.

Antimicrobial coatings may also be added to limit or eliminate infections. These include silver coatings, since silver ions may be active against a broad spectrum of bacteria. Other approaches may include the use of exidine- and silver sulfadiazine-impregnated surfaces, which may reduce the incidence of short-term catheter bloodstream infections. In yet another approach, therapeutic antibiotics may be used, when impregnated intra- and extra-luminally. Exemplary agents include minocylcine, rifampin and tetracycline.

Another strategy may be the use of biomaterial coatings with anti-adhesive molecules such as antifibronectin antibodies, which may block the messengers involved in quorum sensing dependent biofilms.

Finally, another approach for preventing infections may be the use of ultra low fouling zwitterionic-based materials. These coatings may be highly effective at resisting nonspecific protein adsorption from undiluted blood plasma or serum and preventing infection. Specifically, zwitterionic poly(carboxybetaine methacrylate) (pCBMA) and poly(sulfobetaine methacrylate) (pSBMA) grafted surfaces may be used that are highly resistant to nonspecific protein adsorption) from undiluted blood plasma and serum.

The foregoing disclosure of the exemplary embodiments has been presented for purposes of illustration and description. It is not intended to be exhaustive or to limit the invention to the precise forms disclosed. Many variations and modifications of the embodiments described herein will be apparent to one of ordinary skill in the art in light of the above disclosure. For example, elimination of some components, such as the flexible sleeve that deforms in actuation, is possible and within the scope of the present invention. Another method may include allowing the core to rotate and deform the tip of the male Luer without the need for a sleeve. The scope of the invention is to be defined only by the claims appended hereto, and by their equivalents.

Further, in describing representative embodiments, the specification may have presented the method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

I claim:

1. A valve assembly for controlling fluid flow along a fluid line, comprising:
   an outer shell having a through bore, a distal end, and a proximal end;
   an inner housing movably engaged within the outer shell and having a central boss having a through bore with a distal end opening and a connector portion configured for connecting the distal end of the valve assembly in a fluid line;
   a sealing pin coupled to the outer shell and extending into the through bore of the central boss to define a passageway in the central boss around the sealing pin;
   the inner housing being movable relative to the outer shell and sealing pin in a distal direction between a first, closed position and a second, open position on connection of the connector portion to a fluid line; and
   the sealing pin having a distal tip which is configured for sealing engagement in the distal end opening of the central boss through bore to prevent fluid flow through the distal end opening in the first, closed position of the inner housing and which is spaced inwardly from the open distal end of the central boss in the second, open position to open a fluid path through the central boss around the sealing pin and out of the distal end opening.

2. The valve assembly of claim 1, wherein the sealing pin is a solid member having no through bore.

3. The valve assembly of claim 1, wherein the solid sealing pin is formed from an elastomeric material.

4. The valve assembly of claim 3, wherein the distal tip of the sealing pin is configured for sealing engagement in the distal end opening, the through bore of the central boss has a first diameter and the sealing pin has a second diameter less than the first diameter along at least a major portion of its length whereby an annular passaway is formed along at least the major portion of the length of the sealing pin between the sealing pin and the through bore of the central boss, said annular passageway comprising at least a major portion of the fluid path through the central boss in the second, open position of the inner housing.

5. The valve assembly of claim 4, wherein the distal end opening has cross-sectional dimensions smaller than the first diameter and the distal tip of the sealing pin is a press fit in said distal end opening in the closed position of the inner housing.

6. The valve assembly of claim 1, wherein distal tip and distal end opening have mating, tapered sealing surfaces.

7. The valve assembly of claim 1, wherein the inner housing is biased towards the first, closed position on separation of the connector portion from the fluid line.

8. The valve assembly of claim 1, wherein the connector portion surrounds the central boss at a distal end portion of the inner housing and has a set of connector threads surrounding the boss and defining a first helical axis for connecting the inner housing to a mating connector in a fluid line.

9. The valve assembly of claim 8, wherein the central boss and connector portion define a male Luer connector configured for connection to a matching female Luer connector.

10. The valve assembly of claim 8, further comprising a releasable securing mechanism which is configured to engage the mating connector when the inner housing is secured to the mating connector in the second, open position and to prevent the mating connector from disconnecting from the valve assembly until the inner housing moves to the first, closed position.

11. The valve assembly of claim 10, wherein the connector portion and central boss comprise a male Luer connector and the mating connector comprises a female Luer connector for mating, threaded engagement with the male Luer connector, and the releasable securing mechanism comprises a plurality of tines at the distal end of the inner housing and a biasing mechanism configured to bias the tines into locking engagement over threads of the female Luer connector when the inner housing is in the second position and to release the tines to allow the female Luer connector to be separated from the valve assembly when the inner housing moves into the first, closed position.

12. The valve assembly of claim 1, further comprising camming elements between the through bore of the outer shell and the outer surface of the inner housing configured to cause the inner housing to move helically outwards in a distal direction when the connector portion is connected to a mating connector to connect the valve assembly in a fluid line, whereby the inner housing moves from the closed position where the sealing pin engages the distal end opening and the open position where the distal opening moves outwardly and away from the sealing pin to open the fluid path through the valve assembly.

13. The valve assembly of claim 12, wherein the camming elements comprise a set of outer camming threads on the inner housing and a set of inner camming threads on the outer shell together defining a helical axis.

14. The valve assembly of claim 13, wherein the set of camming threads is configured such that the inner housing is directed inwardly to the first, closed position before the mating connector is disconnected from the connector portion.

15. The valve assembly of claim 1, wherein the inner housing is movable between a disconnected and closed condition, a connected and closed condition when the connector portion is engaged with a mating connector in a fluid line with the fluid path through the valve assembly remaining closed, and a connected and open position when the connector portion is engaged with the mating connector and the fluid path through the valve assmebly is open and in communication with the fluid line through the mating connector.

16. The valve assembly of claim 1, further comprising a backing member extending through the proximal end of the shell and having a base coupled to the shell, the sealing pin extending from the base and into the central boss, and the backing member defining a proximal portion of the fluid path through the shell which communicates with the passageway in the central boss around the sealing pin.

17. The valve assembly of claim 16, wherein the backing member and sealing pin are formed integrally.

18. The valve assembly of claim 16, wherein the backing member has a proximal end comprising a connector which is configured to couple the valve to a component of a fluid line.

19. The valve assembly of claim 16, wherein the backing member has a proximal end formed integrally with a component of a fluid line.

20. The valve assembly of claim 19, wherein the component comprises a barrel of a syringe.

21. The valve assembly of claim 16, further comprising a sealing member between the base and inner housing, the inner housing being in sliding engagement with the base, and the sealing member configured to provide a substantially fluid tight seal between the inner housing and base when the inner housing moves between the first and second positions.

22. The valve assembly of claim 1, wherein the inner housing has at least one status indicator which is exposed when the inner housing is in the second, open position and the fluid path is open.

23. The valve assembly of claim 22, wherein the inner housing has a distal end portion which projects out of the distal end of the outer shell in the second, open position, the distal end portion comprising the status indicator.

24. The valve assembly of claim 22, wherein the outer shell has a distal end portion having at least one window, and the status indicator comprises a colored outer surface portion of the inner housing which is aligned with the window in the second, open position of the inner housing.

25. The valve assembly of claim 1, further comprising a peel away seal secured over the distal end of the outer shell prior to connection of the valve assembly in a fluid line, whereby the peel away seal is removed and discarded prior to connection of the distal end of the valve assembly in a fluid line.

26. The valve assembly of claim 1, further comprising a disinfectant medium disposed on or around the tip of the sealing pin.

27. The valve assembly of claim 1, wherein one or more surfaces of the valve assembly exposed along the fluid path are coated with one or more coating materials selected from the group consisting of hydrophilic agents, antimicrobial agents, anti-adhesive molecules, anti-fibronectin antibodies, antibiotics, and ultra low fouling zwitterionic-based materials.

28. The valve assembly of claim 1, wherein one or more surfaces of the valve assembly exposed along the fluid path are impregnated with antimicrobial agents.

29. The valve assembly of claim 1, wherein the central boss has a distal end which does not extend beyond the distal end of the outer shell when the inner housing is in the first, closed position and which extends out of the distal end of the outer shell when the inner housing is in the second, open position.

30. An apparatus for delivering fluid into a fluid line, comprising:
a container having an enclosed interior with fluid therein and an outlet communicating with the interior; and
a valve assembly coupled to the container adjacent the outlet and defining a fluid path from the container when the valve assembly is in an open condition and preventing flow of fluid from the container when the valve assembly is in a closed condition;
the valve assembly comprising an outer shell having a proximal end coupled to the container and a distal end, an inner housing movably disposed within the outer shell and having a hollow central boss with a distal end opening and a connector portion configured for connecting the valve assembly to a connector of a fluid line, and a sealing pin coupled to the outer shell and extending into the central boss to define a passageway in the central boss around the sealing pin forming at least part of the fluid path through the valve assembly;
the inner housing being movable relative to the outer shell and sealing pin in a distal direction away from the proximal end of the outer shell between a first, closed position and a second, open position on connection of the connector portion to a connector of a fluid line; and
the sealing pin having a distal tip which is configured for sealing engagement in the distal end opening of the central boss to prevent fluid flow through the distal end opening in the first, closed position of the inner housing and which is spaced inwardly from the open distal end of the central boss to define the open condition of the valve assembly in the second, open position of the inner housing, whereby a fluid path is provided from the container through the central boss around the sealing pin and out of the distal end opening in the open condition.

31. The apparatus of claim 30, wherein the container is an IV.

32. The apparatus of claim 30, wherein the container is a needleless syringe.

33. The apparatus of claim 32, wherein the syringe has a barrel, the barrel having a hollow extension which extends through the proximal end of the shell and defines part of the fluid path through the shell, the extension having a base within the shell, and the sealing pin extends from the base and into the central boss.

34. The apparatus of claim 30, wherein the sealing pin is a solid member.

35. The apparatus of claim 30, wherein at least the distal tip of the sealing pin is formed from an elastomeric material.

36. The apparatus of claim 35, wherein the through bore of the central boss has a first diameter and the sealing pin has a second diameter less than the first diameter along at least a major portion of its length.

37. The apparatus of claim 30, wherein distal tip and distal end opening have mating, tapered sealing surfaces.

38. The apparatus of claim 30, wherein the connector portion has a set of connector threads surrounding the boss and defining a first helical axis for connecting the inner housing to a mating connector in a fluid line.

39. The apparatus of claim 38, wherein the central boss and connector portion of the inner housing define a male Luer connector configured for connection to a matching female Luer connector.

40. The apparatus of claim 38, further comprising camming elements between the through bore of the outer shell and the outer surface of the inner housing configured to cause the inner housing to move helically between the closed position and the open position when a mating connector is threaded into the connector portion of the inner housing.

41. The apparatus of claim 40, wherein the camming elements are configured such that the inner housing is moved from the open position to the closed position before a mating connector is disconnected from the connector portion.

42. The apparatus of claim 38, further comprising a releasable securing mechanism which is configured to engage the mating connector when the inner housing is secured to the mating connector in the second, open position and to prevent the mating connector from disconnecting from the valve assembly until the inner housing moves to the first, closed position.

43. The apparatus of claim 30, further comprising camming elements between the through bore of the outer shell and the outer surface of the inner housing configured to cause the inner housing to move in said distal direction between the closed position and the open position when a mating connector is secured to the connector portion of the inner housing and the mated connector and inner housing are rotated together, such that the mating connector is secured to the connector portion before the inner housing moves into the open position.

44. The apparatus of claim 43, wherein the camming elements comprise a set of outer camming threads on the inner housing and a set of inner camming threads on the outer shell.

45. A method for opening a fluid path in a fluid line using a valve having a proximal end in communication with a proximal part of a fluid line and a connector portion and comprising an outer shell, an inner housing movably disposed within the outer shell and having a boss at a distal end portion and a passage through the boss to a distal end opening, and a backing member coupled to the outer shell having a sealing pin disposed within the passage through the boss, comprising:
- moving the connector portion of the valve into engagement with a connector of a distal part of the fluid line downstream of the valve with the valve closed and the inner housing in a first position in which a distal tip of the sealing pin is in sealing engagement with the distal end opening to close a fluid path through the valve;
- securing the connector portion to the connector, and
- engaging camming elements between the inner housing and outer shell when the connector portion is secured to the connector to urge the inner housing to move outwardly in a distal direction away from the proximal end of the valve from the first position to a second position in which the distal end of the boss is spaced outwardly and away from the corresponding end of the sealing pin and a fluid passage is formed through the boss which extends between the boss and sealing pin and past the distal tip of the sealing pin inside the passage, and out through the distal end opening of the boss, opening a fluid path from the proximal part of the fluid line through the valve to the distal part of the fluid line.

46. The method of claim 45, further comprising coupling the backing member of the valve to a length of tubing comprising the proximal part of the fluid line prior to moving the connector portion of the valve into engagement with a connector at the distal part of the fluid line, the distal part of the fluid line being selected from one of tubing and a medical device for delivery of treatment fluid to a patient.

47. The method of claim 45, wherein the backing member is coupled to the barrel of a syringe or a container of IV fluid comprising the proximal part of the fluid line, and the distal part of the fluid line comprises a length of tubing or a medical device for delivery of a treatment fluid to a patient.

48. The method of claim 45, wherein the step of connecting the connector portion of the valve with a connector at a distal part of the fluid line comprises engaging a set of inner connector threads on the connector portion with a set of external threads on the connector.

49. The method of claim 48, wherein the connector threads define a first helical axis, and the camming elements comprise a set of camming threads defining a second helical axis opposite the first helical axis, the connector and camming threads configured such that when the connector is threaded into engagement with the inner connector threads, the inner member is automatically directed helically from the first position to the second position to open the fluid path.

50. The method of claim 49, further comprising unthreading the connector from the distal end of the inner housing after delivering fluid via the fluid line, thereby directing the inner housing from the second position to the first position such that the sealing pin substantially seals the outlet opening of the boss and closes the fluid path.

51. The method of claim 50, wherein the connector threads and camming threads are configured such that, when the connector is unthreaded from the one end of the inner housing, the inner housing is directed to the first position before the connector is completely unthreaded from the connector threads.

52. The method of claim 45, further comprising initiating disconnection of the connector from the distal end of the inner housing after delivering fluid via the fluid line while retaining the connector in engagement with the inner housing, and releasing the connector to allow separation from the valve only when the inner housing returns to the first position and the distal end opening is closed and sealed.

* * * * *